(12) United States Patent
Vézina et al.

(10) Patent No.: US 6,420,548 B1
(45) Date of Patent: Jul. 16, 2002

(54) METHOD FOR REGULATING TRANSCRIPTION OF FOREIGN GENES

(75) Inventors: Louis-Philippe Vézina, Neuville; Marc-André D'Aoust, Québec, both of (CA)

(73) Assignee: Medicago Inc., Sainte-Foy (CA)

( * ) Notice: Subject to any disclaimer, the term of this patent is extended or adjusted under 35 U.S.C. 154(b) by 0 days.

(21) Appl. No.: 09/678,300

(22) Filed: Oct. 3, 2000

Related U.S. Application Data

(60) Provisional application No. 60/157,133, filed on Oct. 4, 1999.

(51) Int. Cl.$^7$ .................. C07H 21/02; C07H 21/04; C12Q 1/68
(52) U.S. Cl. ............ 536/24.1; 536/23.1; 536/24.3; 536/24.31; 536/24.32; 536/24.33; 135/6
(58) Field of Search .................. 536/23.1, 24.3, 536/24.31, 24.32, 24.33, 24.1; 435/6

(56) References Cited

FOREIGN PATENT DOCUMENTS

WO       WO 97/30163       *  8/1997

* cited by examiner

*Primary Examiner*—Jeffrey Fredman
(74) *Attorney, Agent, or Firm*—Swabey Ogilvy Renault; France Côté; Christian Cawthorn

(57) ABSTRACT

The present invention relates to a method of regulating the transcription of transgene in genetically-modified organisms. More specifically, the invention relates to the use of expression vectors harboring the coding sequence of a gene of interest under the transcriptional control of promoting sequences for which activity is regulated by the presence of nitrogen.

1 Claim, 3 Drawing Sheets

METHOD FOR REGULATING TRANSCRIPTION OF FOREIGN GENES

This application claims benefit to U.S. Provisional Application No. 60/157,133 filed Oct. 4, 1999.

BACKGROUND OF THE INVENTION (a) Field of the Invention

The invention relates to a method of regulating the transcription of transgene in genetically-modified organisms. More specifically, the invention relates to the use of expression vectors harboring the coding sequence of a gene of interest under the transcriptional control of promoting sequences for which activity is regulated by the presence of nitrogen. Preferably, these constructs are used in transgenic leguminous plants (for example soybean, alfalfa, clover, birdsfoot trefoil, beans, peas, peanuts) where growth is not impaired by lack of mineral nitrogen, and in which induction of expression could be performed at any given time during development, through the addition of a suitable nitrogen source. In a broader perspective, the invention could be used to induce expression of any given transgene through the addition of any nitrogen source, provided that the organism can be grown adequately in the absence of this nitrogen inducer; as an example within the plant kingdom, duckweed (Lemna minor) can adapt to grow either on nitrate or ammonium as nitrogen source; transgenic duckweed could therefore be grown on nitrate as a sole nitrogen source and expression of the transgene triggered by the addition of ammonium, provided that the cassette contains a promoter from a native gene for which expression is turned on by the addition of ammonium. The invention therefore provides a means of regulating the expression of a transgenic trait in any organism through the addition of various nitrogenous inducer.

(b) Description of Prior Art

Nitrogen is a molecule essential to life. All living organism need nitrogen in order to synthesize amino acids, the building blocks of proteins, and nucleotides, the building blocks of nucleic acids. It is Ammonium nitrate is the preferred form of mineral nitrogen provided to crops in the form of fertilizer. Nitrate-nitrogen is first reduced to nitrite and then to ammonium through the activity of a metabolic pathway common to most herbaceous plants. Depending on the species, part or all of the absorbed nitrate will move to leaf cells through the xylem before it is reduced to ammonium. Ammonium, or other reduced forms of nitrogen are also absorbed (although usually at lower rates) by the root system but their assimilation does not require reduction. These newly absorbed ammonium or ammonium-containing molecules join the endogenous pools in the cells which is formed by ammonium cycling through amino acids and other nitrogenous molecules. Some species do not metabolize nitrate-nitrogen easily and therefore cannot rely on nitrate as sole nitrogen source; many coniferous species fall into this latter category. Legumes and other symbiotic plant species form a third large class of nitrogen user within the plant kingdom; they form a metabolic alliance with a microbial organism through which they can fix gaseous nitrogen. This reduced nitrogen is used efficiently by the plant for growth, and therefore, these crops can develop independently of the availability of mineral nitrogen in the soil.

Many microbes and wild plant species will adapt extensively to availability of nitrogen sources and can therefore complete their life cycle in the absence of one molecular form of nitrogen, which they could use exclusively and efficiently if available in another growing environment. As for most assimilatory pathways, nitrogen assimilation is tightly regulated in cells. As an example, the expression of genes encoding nitrate reductase (NaR) and nitrite reductase (NiR), which are responsible for the reduction of nitrate to ammonium, has been extensively described in various microbial and plant species (for a review, see Miflin and Lea, Books 5 and 12 in *The Biochemistry of plants*). Although nitrate is not the only regulatory molecule involved in the control of NaR and NiR expression, its presence is essential to initiate the cascade of transduction that eventually leads to sustained transcription and translation of these genes. It has been shown that expression of NaR and NiR genes is repressed in leguminous plants when they are grown in the absence of mineral nitrogen NiR promoters have been characterized in some plant species (Back et al., 1991, *Plant Molecular Biology* 17:9–18; Sander et al., 1995, *Plant Molecular Biology* 27:165–177). Inducibility of these promoters have also been characterized using marker genes in transgenic plants, where it was shown that availability of nitrate is required for full activation of transcription.

Assimilatory pathways for other nitrogen sources have also been described, and promoters for genes involved in some of these pathways have also been characterized.

Genetic transformation of microbes have been used for more than 15 years to produce useful recombinant molecules, and applications in the pharmaceutical, cosmaceutical and dermaceutical industries are being currently exploited. This technology has expanded from microbes to plants and animals in the last ten years with the development of techniques required to adapt this general concept to complex eukaryotic organisms. Basically a gene encoding for a protein of interest or a gene encoding for an enzyme responsible for a modification of a metabolic pathway that leads to a molecule of interest, is linked in an appropriate fashion to cis-and trans-acting regulatory sequences, and transferred to a target cell where it is incorporated in the molecular machinery (in a transitory or stable fashion). The transgenic cell, or a tissue or organism regenerated from the transgenic cell will then perform transcription and translation of the transgene and therefore be enabled to accumulate the protein of interest or to perform the new metabolic reaction through the activity of the enzyme of interest.

The emerging industry of molecular farming (production of recombinant molecules in animals or crops) is one of the most promising industry of the coming century. Its promise is to provide safe and renewable molecule factories for the industry. Among the applications that are currently developed are the production of low-cost monoclonal antibodies for therapeutic and diagnostic uses, the production of unlimited amounts of hormones, cytokines and other bio-active molecules for the treatment of chronicle or lethal diseases, the production of bio-safe substitutes for various blood components, the production of unlimited amounts of processing enzymes for the food and pulp industry, the production of low-cost enzymes for waste treatments, and the production of safe bio-active molecules for the cosmetic industry.

Limitations to the application of this technology has often come from the inability of transgenic organisms to accumulate adequate amounts of the recombinant product, as a result of low transcription rates, improper splicing of the messenger, instability of the foreign mRNA, poor translation rates, hyper-susceptibility of the recombinant protein to the action of endogenous proteases or hyper-susceptibility of the recombinant organism to the foreign protein which result in improper and limited growth or in the worst cases, in strong deleterious effects to the host organism. Inadequacy of production level has a direct impact on the development of applications when profit margins are narrow, or when treatment and/or disposal of residual matter causes bio-safety or environmental problems. Improvement of the accumulation level of the desired recombinant product thus appears to be one critical factor that warrants commercialization of many applications of molecular farming.

The use of inducible promoters has been proposed, and in some instances used successfully, to counteract the combined effect of all the above-mentioned factors. Strong inducible promoters may succeed in generating high ephemerous transcription rates which result in high transitory accumulation of foreign mRNA and translational product. As a result, when inducibility of expression is paired with adequate synchronized protein recovery procedures, the yield per unit obtained is higher than with the use of constitutive expression.

Several expression cassettes harboring inducible promoters have been developed for microbial production systems, and some are currently available for research purposes. Some inducible promoters are currently used in plant (wound inducibility) or animal (specificity to cells of the mammary glands, PPL) systems, although none reported are using low-cost and bio-safe chemical inducers such as nitrate salts.

It would be highly desirable to be provided with a method of regulating the transcription of transgene in genetically-modified organisms.

SUMMARY OF THE INVENTION

One aim of the present invention is to provide a method of regulating the transcription of transgene in genetically-modified organisms.

Another aim of the present invention is to provide the use of expression vectors harboring the coding sequence of a gene of interest under the transcriptional control of promoting sequences for which activity is regulated by the presence of nitrogen.

The present invention relates to the use of a nitrogen-inducible expression cassettes for the controlled expression of foreign genes in plants. It will be shown from the following description that isolating such a regulatory sequences can be performed so that when cis-acting sequences are appropriately associated to the open reading frame of a gene of interest, its transcription can be controlled by the addition of specific nitrogen sources.

In one aspect of this invention, the targeted system uses leguminous plant species, so that constructs containing a nitrate-inducible promoter will be maintained transcriptionally low throughout the growth period if the transgenic plant is maintained on a nitrate-free medium, thus allowing the development of the plant biomass without interference from the transgenic trait. Upon addition of nitrate to the growth medium, transcription will be induced in a relatively large proportion of the biomass over the following days. Optimization of induction time and protein accumulation will then be performed in order to maximize recovery of the desired recombinant product.

Although the following description will make clear that this invention can be easily adapted to nitrate induction on nitrate-deprived transgenic leguminous plants, it should be remembered that this general concept can also be applied to the development of other production systems, making profit of the wide variety of nitrogen assimilation systems in the microbial, plant and animal kingdoms.

In one other aspect of this invention, nitrogen inducibility can also be used to maximize protein production in organisms which do not perform nitrogen fixation through symbiotic association, but that can use variable sources of nitrogen (reduced or oxidized) for growth, and thus possess the ability to develop adequately while one of their nitrogen assimilation pathway is inactive due to lack of one nitrogenous substrate in the growing environment. Using an expression cassettes that controls the transcription of any gene in this inactive pathway in order to drive the expression of a gene of interest in such an organism, will allow for inducible expression of the transgenic trait upon addition of the previously lacking nitrogenous compound. As an example, duckweed is a plant species that can grow alternately on nitrate or ammonium; this invention could be used to develop an expression cassette harboring an ammonium-inducible promoter appropriately linked to a gene of interest so that the induction would be performed on nitrate-grown transgenic duckweed plants.

In accordance with the present invention there is provided a method for regulating transcription of a foreign gene in transgenic organisms, comprising the steps of:

a) preparing a transgenic organism using an expression construct consisting of at least a nitrogen-inducible promoter having a sequence selected from the group consisting of SEQ ID NOS: 1 to 13 and functional fragments and derivatives thereof, and an ORF of a gene, wherein said promoter is operationally located with respect to said gene for expression of said gene.

In accordance with a preferred embodiment of the present invention, the method of may further comprise the step of regulating transcriptional expression of said gene by addition or removal of a nitrogen inducer.

In accordance with a preferred embodiment of the present invention, there is provided a method for regulating transcription of a foreign gene in transgenic organisms comprising:

a) preparing an expression construct consisting of at least a nitrogen-inducible promoter with or without cis-acting sequence, an ORF of a gene, and a polyadenylation signal end site at the 3'end of said construct, wherein said promoter is operationally located with respect to said gene for expression of said gene and modulated for transcriptional expression of said gene by addition or removal of a nitrogen inducer;

b) sub-cloning the construct of step a) into a suitable transfection vector for said organism;

c) transferring said vector into DNA of said organism or a cell thereof; and d) selecting for transgenicity on a suitable medium.

In accordance with a preferred embodiment of the present invention, the method of may further comprise the steps of:

e) introducing the vector into a suitable *Agrobacterium tumefaciens* strain;

f) using the Agrobacterium strain of step a) to transfer T-DNA into a plant cell;

g) selecting for transgenicity of said plant cell on a suitable medium;

h) regenerating embryos or plantlets from said transgenic cells; and i) growing mature plants from said regenerated embryos.

In accordance with a preferred embodiment of the present invention, the cis-acting sequence may be isolated from 5' upstream region of an expressed Nir gene in alfalfa.

In accordance with a preferred embodiment of the method of the present invention, the promoter has the sequence set forth in SEQ ID NO:1 to 13 and functional fragments and derivatives thereof.

In accordance with a preferred embodiment of the present invention, the organism is a plant, more preferably a dicotyledonous plant.

In accordance with a preferred embodiment of the present invention, the organism is alfalfa or tobacco.

In accordance with a preferred embodiment of the present invention, the nitrogen inducer is nitrate.

In accordance with a preferred embodiment of the present invention, the DNA transfer method is any suitable transfer method including DNA bombardment, electroporation, PEG-mediated DNA transfer and whiskers, among others.

In accordance with a preferred embodiment of the present invention, the expression construct comprises at least a nitrogen-inducible promoter and at least one cis- or trans-acting elements.

In accordance with a preferred embodiment of the present invention, the organism is a plant, a fungus, a bacteria, a yeast or an animal.

In accordance with a preferred embodiment of the present invention, the promoter or cis-acting sequence is isolated from the 5' upstream region of any gene involved in a nitrogen assimilatory pathway.

In accordance with a preferred embodiment of the present invention, the promoter or cis-acting sequence is isolated from the 5' upstream region of any gene for which transcription is modulated by availability of a given nitrogen source.

In accordance with a preferred embodiment of the present invention, the promoting or cis-acting sequence is any sequence for which transcriptional activity is regulated by addition or removal of any nitrogen source in or from any living organism's environment.

In accordance with a preferred embodiment of the present invention, the organism from which the promoter or cis-acting sequence is isolated from is any plant, fungus, yeast, bacteria or animal.

In accordance with a preferred embodiment of the present invention, there is provided a promoter for promoting transcription of a foreign gene in transgenic organisms, which comprises a nitrogen-inducible promoter with or without cis-acting sequence for expression of said gene and adapted to be modulated for transcriptional expression of said gene by addition or removal of a nitrogen inducer.

Preferably, the promoter has a sequence selected from the group consisting of SEQ ID NOS: 1 to 13 and functional fragments and derivatives thereof.

In accordance with a preferred embodiment of the present invention, there is provided a terminator allowing expression of a foreign gene in transgenic organisms being used in combination with a promoter, which comprises a polyadenylation signal end site for insertion at the end of said gene, wherein said terminator is operationally located with respect to said gene and said promoter and thereby allows expression of said gene.

Preferably, the terminator has a sequence selected from the group consisting of SEQ ID NOS: 14 to 16 and functional fragments and derivatives thereof.

For the purpose of the present invention the following terms are defined below.

The expression "functional fragments or derivatives thereof" is intended to mean any derivative or fragment of sequences SEQ. ID. NOS:1–16 which allow for an equivalent level of expression of a foreign gene as the promoter of the present invention set forth in SEQ. ID. NOS:1–13 or as the terminator of the present invention set forth in SEQ. ID. NOS:14–16.

DETAILED DESCRIPTION OF THE INVENTION

Figure 1:
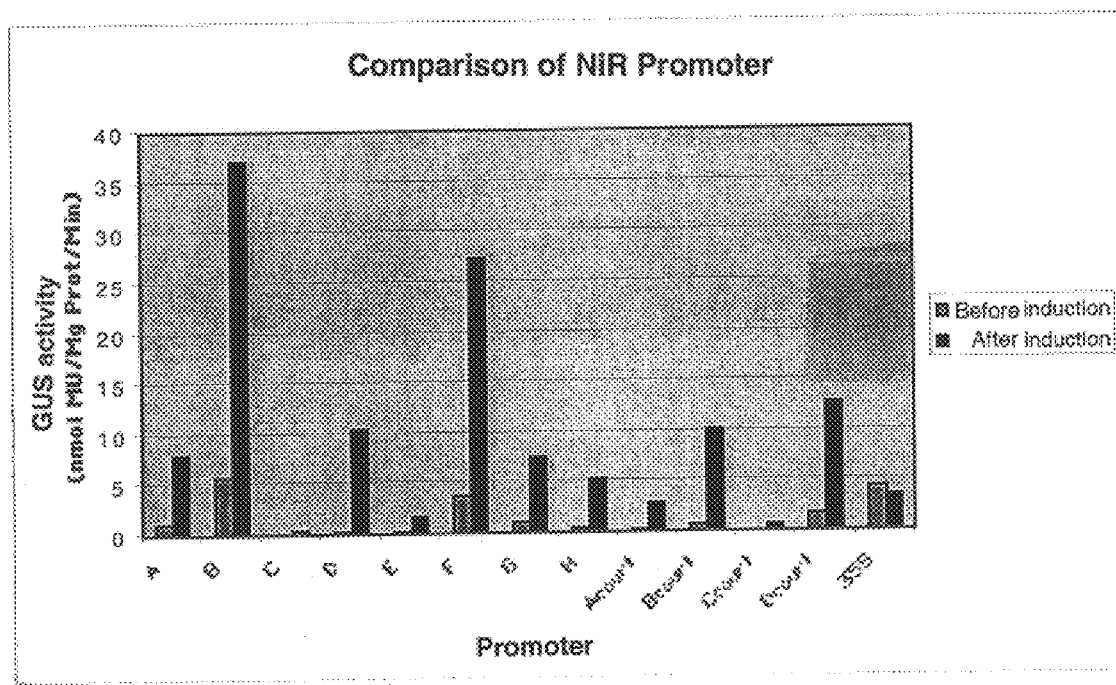
FIG. 1 illustrates GUS expression level using promoter Nir (SEQ ID NOS:2–13) and terminater NOS in the leaves of transgenic tobacco plants before (empty columns) and after (filled columns) nitrate fertilization of the plants. Tobacco plants were transformed with full-length and deletions of the alfalfa NiR promoter and NOS terminator functionally positioned to control transcription and terminaison of the GUS reporter gene, as described in Methods. GUS activity was measured according to Jefferson et al. (1987, *EMBO J.* 13:3901–3907) prior and after induction by nitrate.

Following is a detailed description of the method used to generate transgenic tobacco and alfalfa lines that can be modulated in their expression of a reporter gene. It should be remembered that variations could be brought to the method by which nitrogen-inducible promoters could be isolated, by which they could be linked to ORFs in the construct used for expression in plants, by which different cis- and transacting elements of the constructs are used and spatially arranged, by which the inducibility by nitrogen is demonstrated and used, while remaining within the scope of this invention.

In this embodiment, a NiR cDNA strand was first isolated from alfalfa using RT-PCR with primers deduced from a consensus plant NiR sequence. This cDNA stretch was then used either to perform upstream/downstream genome walking. The NiR promoter region and deletions, the 5'UTR and the NiR terminator were then positioned functionnally to control transcription and terminaison of reporter gene GUS. These constructs were inserted into suitable expression vectors for DNA bombardment onto tobacco and alfalfa leaves and for Agrobacterium mediated DNA transfer as described by Desgagnés et al. (1995, *Plant Cell Tissue Organ Cult.* 42:129–140). These two DNA transfer methods were used to demonstrate that expression of the reporter gene can be modulated by addition or removal of nitrate in the growing medium.

Materials and Methods
Biological Material

*E. coli* strain DH5-α was used to perform all cloning steps. Cold resistant alfalfa genotype 11.9 was used for all experiments including stable transformation using A. tumefaciens infection (Desgagn és et al. (1995, *Plant Cell Tissue Organ Cult.* 42:129–140).

Isolation of Total RNA

Total RNA was extracted using a hot phenol method essentially as described by de Vries et al. (1988, B6 page 1, In: Gevin SB and Shilperoot RA editors, Plant Molecular Biology Manual, Dordrecht: Kluwer Academic Publisher).

RT-PCR

RT-PCR was used to produce a DNA fragment corresponding to one abundant NiR mRNA molecular species from leaf total mRNA. A conserved region was first identified from 5 public plant NiR ORFs, namely Genbank sequences #AB006032 (Arabidopsis Nir mRNA), # X66145 (Tobacco partial Nir mRNA), #U10419 (Bean complete Nir cds), #X07568 (Spinach Nir mRNA), and #U90429 (Glycine max Nir complete cds). Degenerated oligonucleotides were deduced from two conserved regions, namely Nir5-5' GATATTGATGTTAGACTCAAGTGGC 3' (SEQ ID NO:17), at the 5' end and Nir3-5' CACYSATTCCACT-TCCTWGGC 3' (SEQ ID NO:18), at the 3' end of the coding strand. A reverse transcription reaction was first performed with 200 units of M-MLV reverse transcriptase (RT) for 1 hour at 37° C. using 1 μg of total leaf RNA, 4 mM dNTP (1 mM each), 5 μM random hexamer primers in a 1× M-MLV-RT buffer (50 mM Tris-HCl pH 8.3, 75 mM KCl, 3 mM $MgCl_2$). The PCR reaction was performed in a Perkin Elmer Cetus GenAmp PCR system 9600 (EG&G, Wellesley, Mass.), using 2.5 units of Taq DNA polymerase, 2 μM Nir5 primer, 2 μM Nir3 primer, 800 μM dNTPs (200 μM each) in a 1× PCR buffer (20 mM Tris-HCl pH 8.4, 50 mM KCl, 2 mM $MgCl_2$). The cycling program used was: an initial 4 min at 94° C., 30 cycles of 1 min at 94° C., 30 sec at 55° C., and 3 min at 72° C. An extension period of 7 min at 72° C. was included in the program.

DNA Sequencing

DNA sequencing was performed as described by Sanger et al. (1977, *P.N.A.S. USA*, 74:5643–5647).

Genome Walking

Walking upstream of the Alfalfa Nir cDNA fragment cloned from the RT-PCR reaction was performed using the Universal Genome Walker Kit from Clontech Laboratories (Palo Alto, Calif.) (Cat. #1807-1). The NiR-specific custom primers used to amplify sequences upstream of the coding sequence were:

Nir1106r-5' TTGTCACATCAGCACATCCGTCTTTGC 3' (SEQ ID NO:19), and

Nir106r-5' TCGCCMGTATCTTGTTTGAGCACTTG 3' (SEQ ID NO:20).

The amplified 3775 bp fragment was subcloned into pGEM-T Easy vector (Promega, Madison, Wis.) (Cat #A1360) for further analysis. The resulting plasmid was named pGNir4c.

The downstream walking was performed as the upstream walking using the following NiR specific primers:

Nir1c-5' ATGTCTTCCTTCTCAGTACGTTTCCTC 3' (SEQ ID NO:28), and

Nir138c-5' CMGTTGATGCATCMGGTGGGAGCCTAGA 3' (SEQ ID NO:29).

The amplified 3508 bp fragment was subcloned into pGEM-T easy vector (Promega, Madison, Wis.) (Cat #A1360) for further analysis. The resulting plasmid was named pGN3'1.

Construction of Expression Cassettes and Vectors

The cassettes for expression analysis using the GUS reporter gene were assembled as follows. A promoterless GUS cassette was digested from pBI101 with HindIII and EcoRI, and was inserted into the HindIII and EcoRI sites of the pUC19 polycloning site. The resulting plasmid was named pBI201 and was used for further constructs. The Nir upstream sequences were PCR amplified using the AP2 primer from the Universal Genome Walking Kit as upstream positioned primer, and either one of custom-designed downstream primers ending with a SmaI restriction site. The 4 primers were positioned either in the 5' UTR region of the gene (Nir-23r-Sma-5'AGAGCCCGGGAGMGAGAGTGTGTTTG3' (SEQ ID NO:21)), at the end of the transit peptide coding sequence (Nir51r-Sma-5' TTCTCCCGGGGGACGAGAGATG-GATGGT 3' (SEQ ID NO:22)), 50 bp after the transit peptide coding sequence (Nir103r-Sma-5' TTCTCCCGGGGTTGM-ACAGGTGCMCTGA 3' (SEQ ID NO:23)), and 100 pb after the transit peptide coding sequence (Nir158r-Sma-5' TTCTCCCGGGTMC-CATCTTTTTCCTCA 3' (SEQ ID NO:24) Amplification was performed under standard conditions with pGNir4c plasmid as template.

The amplified fragments were digested with specific restriction enzymes in order to produce 5' deletions of the Nir promoter. The pNir3k-23 was produced by digesting the fragment previously amplified by AP2 and Nir-23r-Sma primers with XmaI, and inserting the resulting fragment into pBI201 previously digested with XmaI. A similar strategy was used to produce the pNir3k51, pNir3k103, and pNir3k158 plasmids except that the downstream primers used were Nir51r-Sma, Nir103r-Sma, and Nir158r-Sma, respectively. The pNir2.2k-23 was produced from a SmaI-BglII digestion of the AP2 -Nir-23-Sma amplified fragment inserted into the pBI201 previously digested with SmaI and BamHI. The same strategy was used to produce the pNir2.2k51, pNir2.2k103, and pNir2.2k158 plasmids except that the downstream primers used were Nir51r-Sma, Nir103r-Sma, and Nir158r-Sma, respectively. Fidelity and orientation of the insertions were verified by digestion with restriction enzymes. These deletion fragments were ligated to the 5'terminus of the GUS reporter gene in pBI201, and used for transitory expression studies using DNA bombardment. Upon identification of the adequate deletion fragments, they were sub-cloned into a binary plant expression vector such as pBI101 (Clonetech).

For the construction of the cassettes containing the NiR terminator downstream of the GUS gene in addition to the NiR promoter, the following NiR specific primers were used:

Nir2514c-Sac-5' AGAAGAGCTCAGTATATAGG-TATTTGGTGA 3'(SEQ ID NO:30)

Nir2728c-Sac-5' AGMGAGCTCTTGTACATTTG-GATAAGTCA 3' (SEQ ID NO:31)

Nir3029r-Eco-5' AGMGMTTCGTTTTCCCGATACTTC-MCT 3' (SEQ ID NO:32)

A 617 bp terminator fragment was PCR amplified using the primers Nir2514c-Sac and Nir3029r-Eco, and a 503 bp terminator fragment was PCR amplified using the primers Nir2728c-Sac and Nir3029r-Eco. The fragments obtained were digested with SacI and EcoRI and inserted into the plasmids containing the NiR-GUS constructs after deletion of the NOS terminator between the SacI and EcoRI sites.

These recombinant plasmids were used for stable integration through *A. tumefaciens* infection as described below. Agrobacterium-mediated DNA Transfer and Regeneration of Transgenic Alfalfa Lines The recombinant plasmids were introduced into *Agrobacterium tumefaciens* strain LBA4404 by electroporation as described in Khoudi et al (1997, *Gene* 197:343–351). Selected Agrobacterium strains were then co-cultivated with leaf disks from genotype C5-1 for 4 days in the absence of selection pressure (kanamycin). Following this incubation period, leaf disks were washed and pampered, and then allowed to form calli onto medium B5H. Calli were then transferred for 21 days on SH medium for embryo induction and for 28 days on BOi2Y for embryo development. Torpedo-shaped embryos were removed from Boi2Y and placed on MS medium for regeneration. Kanamycin was present in all cultivation medium except for co-cultivation and regeneration on MS. This method is described in length in Desgagnés et al (1995, *Plant Cell Tissue Organ Cult.* 42:129–140). Rooted plantlets were grown to maturity in the greenhouse. Integration of the transgene was verified by PCR amplification of a NiR-GUS fragment from genomic DNA. The primers used were:

Nir-102c-5' CACACTTCTTCACTCACCTCTCAA 3' (SEQ ID NO:25)
Nir-2016c-5' ATCTAGGAGGGGCAGACATTG 3' (SEQ ID NO:26)
GUS228r-5' TCGGTATAAAGACTTCGCGCTGAT 3' (SEQ ID NO:27)

Agrobacterium-mediated DNA Transfer and Regeneration of Transgenic Tobacco Lines The recombinant plasmids were introduced into Agrobacterium tumefaciens strain LBA4404 by electroporation as described in Khoudi et al (1997, *Gene* 197:343–351). Selected strains were co-cultivated with leaf disks for 2 days on MS medium without kanamycin. After this period, the explants were transferred to the selection medium (MS with Kanamycin). The explants were kept on this medium for 3 weeks to allow the formation of calli and shoots from the transfected cells. The kanamycin resistant shoots were transferred into the rooting MS medium. Rooted plantlets were grown to maturity in the greenhouse. Integration of the transgene was verified by PCR amplification of a NiR-GUS fragment from genomic DNA. The primer used were:

Nir-102c-5' CACACTTCTTCACTCACCTCTCAA 3' (SEQ ID NO:25)
Nir-2016c-5' ATCTAGGAGGGGCAGACATTG 3' (SEQ ID NO:26)
GUS228r-5' TCGGTATAAAGACTTCGCGCTGAT 3' (SEQ ID NO:27)

Nitrate Induction

Transgenic and non-transgenic tobacco and alfalfa plants were grown in vermiculite medium without nitrate. Mineral balance was kept by repeated additions of nitrate-free Hoagland's solutions (Hoagland and Varnon, 1950, Circular 347, *California Agr. Exp. Stat. Berkeley*). Nitrate induction was performed by watering the plants with 20-20-20 fertilizer at a concentration of $5gL^{-1}$ or as an alternative with Hoagland's solution supplemented with 40 mM nitrate.

NiR Promoter Activity in Tobacco Leaves

The NiR derived promoters were placed upstream of the GUS reporter gene in transcriptional and translational fusions. The 5' deletions of the NiR promoter analyzed here consisted in (1) a putative full length promoter comprising 2813 bp upstream of the initial ATG of the coding region, (2) a 1905 bp version of the promoter, and (3) a shorter 1111 bp version of the promoter. The 3' end of the promoter was fused to the 5' end of the GUS coding region to form transcriptional and translational fusions. Translational fusions analyzed allowed the production of β-glucuronidase containing (1) the NiR chloroplast transit peptide, (2) the NiR transit peptide with an additional 17 amino acids from NiR, and (3) the NiR transit peptide with an additional 36 amino acids from NiR. The twelve combinations of 5' and 3' deletions of the NiR promoter introduced into tobacco plants are presented in FIG. 1.

The gene constructs were transferred into tobacco plants using the Agrobacterium-mediated transfection method (Khoudi et al., 1997, *Gene* 197:343–351). Transgenic plants were transferred to growth chambers and analyzed for their leaf β-glucuronidase content before and after nitrate fertilization. FIG. 1 presents the median level of β-glucuronidase activity measured in the $1^{st}$ expanded leaf of plantlets.

All the NiR derived promoters showed reactivity to nitrate induction. Between 5 and 10 fold increase of β-glucuronidase expression was generally observed, irrespectively of the promoter truncation, indicating that important nitrate responsive elements are contained within the first 1.1 kb upstream of the initial ATG. Both 5' and 3' deletions of the NiR promoter led to important modifications of β-glucuronidase activity. The highest level of GUS expression was obtained with the 2.8 kb promoter, indicating that the far upstream regions have a regulatory role for the level of NiR expression in the leaves.

The translational fusions of the promoter to the GUS coding region resulted in variable expression level depending on the extension of the 5' end of the promoter. However, the shortest fusion (containing the 17 a.a. NiR transit peptide fused to the amino-terminal end of the β-glucuronidase) constantly resulted in the highest level of activity for all three 5' end truncations. This short translational fusion, combined with the longest extension of upstream promoter regions gave rise to the strongest promoter (3 kb+50). When induced, this specific construct resulted in more than 13-fold the level of GUS expression obtained with the 35S-GUS-NOS construct.

When considering the longest 5' extension of the promoter, the transcriptional fusion to the GUS gene (3kb-5) was ~7 times less effective than the short translational fusion (3kb+50). However, in it's induced state, the level of GUS expression in the plants harboring the 3kb-5 promoter deletion was more than 1,8-fold that observed in the 35S-GUS-NOS plants.

Taken together, the results presented here clearly indicate that the sequences upstream of the alfalfa NiR gene have the capacity to drive high and inducible expression of an exogenous gene in tobacco leaves.

Efficiency of NiR Terminator

Figure 2:
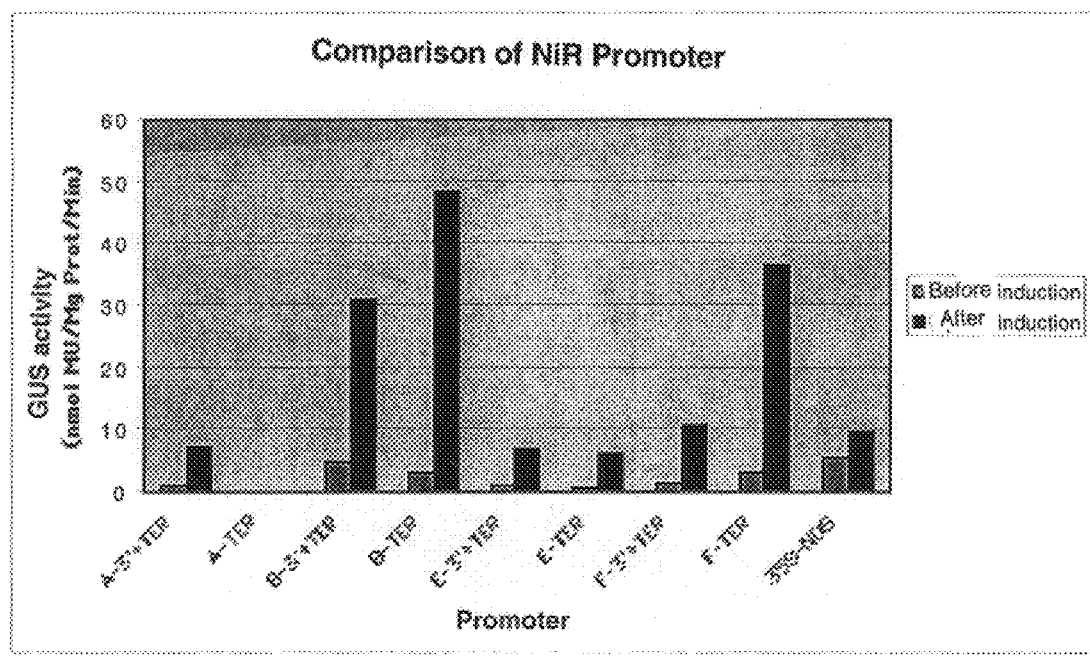
FIG. 2 illustrates GUS expression level using promoter Nir (SEQ ID NOS:2, 3, 5–6) and terminater Nir (SEQ ID NOS:15–16) in the leaves of transgenic tobacco plants before (empty columns) and after (filled columns) nitrate fertilization of the plants. Tobacco plants were transformed with full-length and deletions of the alfalfa NiR promoter and NiR terminator functionally positioned to control transcription and terminaison of the GUS reporter gene, as described in Materials and Methods below. GUS activity was measured according to Jefferson et al (1987, *EMBO J.* 13:3901–3907) prior and after induction by nitrate.

Tobacco plants were transformed with constructs consisting of promoter NiR and deletions (SEQ ID NOS: 2, 3, 5 and 6), and 35S, together with 3'UTR sequences and terminator (SEQ ID NOS: 15 and 16), functionally positioned to drive transcription and termination of reporter gene GUS. Growth, nitrate induction and GUS activity measurements were performed as per experiment illustrated in FIG. 1. Results shown in FIG. 2 demonstrate that the terminator sequence of Nir allows termination of transcription into a translatable messenger RNA.

NiR Promoter Activity in Alfalfa Leaves

Figure 3:
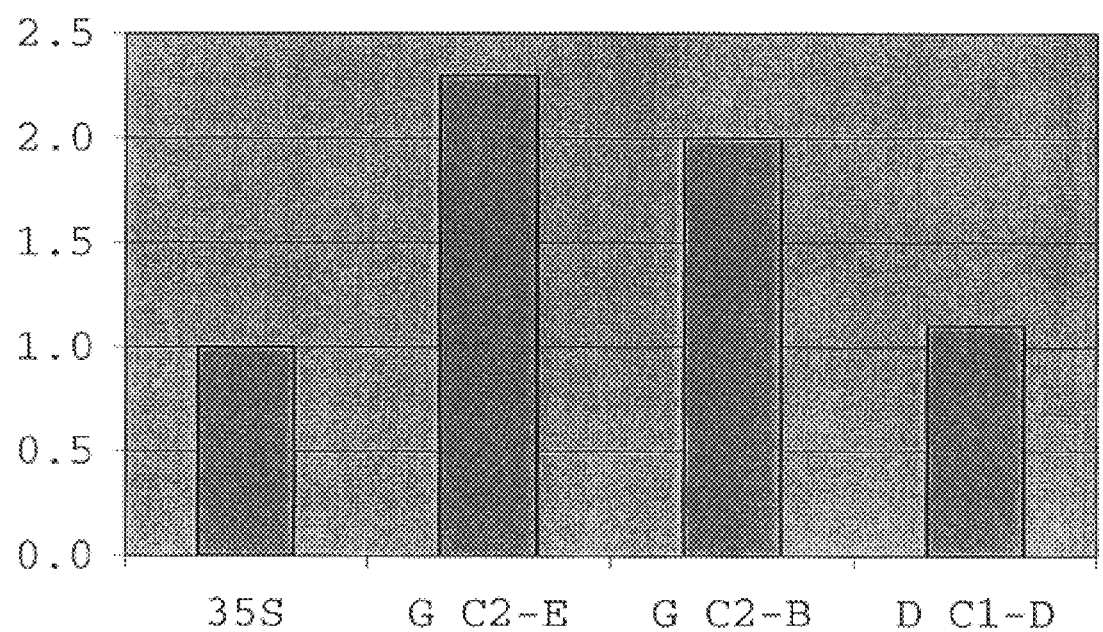
FIG. 3 illustrates GUS expression level using promoter NiR and terminator NOS in the leaves of nodulated transgenic alfalfa plants before (empty columns) and after (filled columns) nitrate fertilization. Alfalfa genotype 11.9 was transformed with constructs GC2-E, GC2-B, DC1-D and 35S functionally positioned to drive expression of reporter gene GUS, as described in Khoudi et al (1997, *Gene* 197:343–351). Following regeneration, transgenic plants were transfered to sterile vermiculite and inoculated with Rhizobium strain Balzac (Nitragin). Plants were allowed to grow for 3 weeks with repeated additions of nitrate-free Hoagland's solution; GUS activity was then measured in first fully expanded leaves as described by Jefferson et al. (1987, *EMBO J.* 13:3901–3907). Plants were then fertilized with 40 mM nitrate for two days. GUS activity was again measured in first fully-expanded leaves. Data shown herein are ratios between post- and pre-nitrate induction GUS specific activities.

Transgenic alfalfa plant containing the gene constructs presented in FIG. 3 were obtained using the Agrobacterium-mediated transfection method of Desgagn és et al. (1995, *Plant Cell Tissue Organ Cult.* 42:129–140). The in vitro plants were transferred into growth chamber to allow a normal vegetative growth. Cuttings from each transgenic line were grown in vermiculite and fertilized with nitrate-free Hoagland medium. After two weeks, the roots were inoculated with Nitragin (Lipha Tech inc., Milwaukee, Wis.). Two weeks after inoculation, nodules had developed on the roots. Nodulated plants were allowed to continue their vegetative growth for at least another week before the fluorometric measurement of β-glucuronidase activity (before induction) was performed. After the measurement, the plants were watered with Hoagland medium containing 40 mmol $KNO_3$. Two days after induction, leaf β-glucuronidase activity was measured to evaluate the nitrate inducibility of the NiR promoter in alfalfa leaves. Results are presented in FIG. 3. Results show that promoter NiR induces expression of GUS reporter gene upon addition of nitrate in nodulated alfalfa plants. Taken together, this last series of result demonstrate that NiR promoter inducibility can be used to positively regulate expression of a foreign gene in alfalfa plants when fixation of atmospheric nitrogen is replaced by nitrate assimilation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated promoter for promoting transcription of a foreign gene in transgenic organisms, which comprises a nitrogen-inducible promoter with or without cis-acting sequence for expression of said gene and adapted to be modulated for transcriptional expression of said gene by addition or removal of a nitrogen inducer, said isolated promoter having the nucleic acid sequence as depicted in SEQ ID NO:11.

* * * * *

SEQUENCE LISTING

```
<160> NUMBER OF SEQ ID NOS: 32

<210> SEQ ID NO 1
<211> LENGTH: 3714
<212> TYPE: DNA
<213> ORGANISM: Artificial Sequence
<220> FEATURE:
<223> OTHER INFORMATION: Sequences to be used as promoter for regulating
      expression of foreign genes

<400> SEQUENCE: 1
ctgtacattc atcttgccgc ctttgcattc acttggccac aaagagtaga gagaaggaag      60
agaagagccc agacttcaag aagcgacctt gcaagtgcac tcgagggtca gaaactgtat     120
atcatatcta tgtgagagaa aggggaacat ttgagatgga gtccatttac ttgaggtata     180
cttattattt tgatcaataa atttgtatac ttcttattta gatcaataaa tttgtcatta     240
agctataatc caaaataaat tacgatcaaa tatgcaaatg ttagccagta cttgtgttaa     300
acttgatggc atctcttggt ttctttggca atcacatgcc taagaaataa atagtatcat     360
atgattgtgt ttggtcagac ttcagagtca gatgactctg tttggataaa cagcttaatt     420
aagcgcttat agaatatcat atgattgtgt ttggtcagac ttcagagcat ctcttggttt     480
ctctggcaat catatgccta agaaataaat agtatcatat gattgtgttt ggtcagactt     540
cagagtcaga tgaccctgtt tgggtaaaca gcttaattaa gtgcttatag aataagcgct     600
tatcatataa gtgcttttgt acagttattt ctatgaaagt agaagaaata gtcatattgt     660
tttaatataa gctatcctgg agagcttgtg gaaataacca gaaaagaact tatggacacg     720
tcatgagctg tttacataag atctccctaa cagtctcaaa agtgtttatg ccagtagata     780
aattcaaata agtcaatcta aacagaccct aaatccatta tggtacctat cattttagct     840
tattccatct ttattaagaa tgtcatgaga taacataatg ataacacatt attttgacac     900
aaatgggcag atctagcaat ttaactctgg agtccttcaa gactgctgtt cttacgaagt     960
tcacgtccct gaatcatgtt cctgtatgga agcctgaaag acctcaaatt ctaaaaggtg    1020
gcgataaatt gaaggtttac aaaatatacc ctgcgggctt gacacagagg caagctcttt    1080
ataccttcca gttcaacggg gatgttgatt tcagaagtca cttggagagc aatccttgtg    1140
ccaagtttga agtaattttt gtgtagcata tgttgagcta cctacaattt acatgatcac    1200
ctagcattag ctctttcact taactgagag aatgaagttt taggaatgag tatgaccatg    1260
```

```
gagtcggcat ggctttgtaa tgcctaccct actttggcca actcatcggg gatttacatt     1320
cagaaaatat acatgacttc aaccatactt aaaccccttt ttgtaagata actgaatgtt     1380
catatttaat gttgggttgt agtgttttta cttgattata tccagacagt tacaagttgg     1440
acaacaagat tgtgggtctg tactgttatt tatttatttt tttttttagca gaaacacctt     1500 atcttttgtt tcgtttgaat gtagaatgaa aataaaagaa agaaaatata acatcatcgg     1560
ccgcgcttgt ctaatttcgg gcagttagga tcctctccgg tcaccggaaa gtttcagtag     1620
aagaaacaaa acaccgtgac taaaatgata ctattatttt atttattgtg tttttctttt     1680
ttctaccgga actttttaga acggatccca actcgttccg gggccgctac aactgaaaca     1740
aaagaagata ttttctctct cttcagaaat gtaagttttc ctttacagat acccattcac     1800
catttgattc agatgtggtg actagagata aagcatacta atttgactct ggaaaccca     1860 taaagtttat gttatccgtg ttctggacca atccacttgg gggcataacc tgtgtctatg     1920
tgtggtttgg tttccattct gatttatgcg gcgacttgta atttaaaatc taggaggggc     1980
agacattgaa caatcccaat attttaataa cttatgcaag attttttttta ttaatgagat     2040 gatgtgtttg tgactgagat tgagtcatac atttcactaa gaaatggttc caagtaccaa     2100
actatcatga cccagttgca aacatgacgt tcgggagtgg tcactttgat agttcaattt     2160
catcttggct tcttattcct tttataattc taattcttct tgtgtaaact atttcatgta     2220
ttatttttct ttaaaattta catgtcattt attttgcctc actaactcaa ttttgcatat     2280
aacaatgata agtgatattt tgactcacaa aatttacatc aaatttcgac atcgtttatt     2340
atgttcattg gatgattaac aaatataaca aactttgcaa ctaattaacc accaactgaa     2400
tataattaac tataactgtg aaagtagtta accatatttt ttagatgtat atatcatccg     2460
ttgaatgtaa ttattcatat atttgaacta agttaccctca aacttaaag aacttaaaga     2520 actcggtttg agacctgggg acgaaaatgt aatgagactt taatgttgac tttgacaccg     2580
caccacatgt gcctttttaca tatagtttat atgacaagta atgacaatcc ttgctctatt     2640
ataaggcgac ccttagctcc aaccaaagga cgatggagtt aagaaagaaa ctcttgctta     2700
cttgtaaggt ccacacttct tcactcacct ctcaatttca tcctacaaaa atgtccaaac     2760
ttctctttct cacaatcaca aactcattcc aaacacactc tcttctccaa aaatgtcttc     2820
cttctcagta cgtttcctca ccccaccatc catctctcgt cccaacaaaa catggctact     2880
atctgctgca actccatcag ttgcacctgt ttcaacacca caagttgatg catcaaggtt     2940
ggagcctaga gttgaggaaa aagatggtta ctgggttttg aaggaagagt atagaggggg     3000
tattaatcct caggagaaag ttaagattca gaaagaacct atgaagcttt ttatggaagg     3060
tgggattaat gatttggcta atatgtctct tgaagagatt gaaagctcta agcttactaa     3120
agatgatatt gatgttagac ttaaatggct tggtcttttt catagaagga aacatcattg     3180
taagtttttt taccttcttt ttatacctca aagttctctc atactctgta tttgtttatt     3240 agttttgta gacttaaata ttctctttga tttacatagt gaaactccat ttttgtttcc     3300
gaaattgtag tgtgtatagt ctagaaaatt aagaagtaga caaaatgatt tatgagattg     3360
taaattgtag gcttttatc aatttattaa ttttagagac caaaatttgc ctatcttatt     3420
tggaccaata ttgtatgtca ggatcgacat gagtttagta aaatcatgac ggcaccatga     3480
ctgtgttgaa gcttctttgt gtaactttaa ccaaaattat atggcacacc ataattatgc     3540
aaactcaccg tcgatccaaa catagaaatt cggtgttaat ctttgtgaga ataaaaagct     3600
atgagttatg ttgtactaat ttatttccat tgtgaaaatc agatggtaga tttatgatga     3660
```

-continued gactgaaact tccaaatggg gtaacaacaa gtgctcaaac aagatacttg gcga         3714

<210> SEQ ID NO 2
<211> LENGTH: 2808
<212> TYPE: DNA
<213> ORGANISM: Artificial Sequence
<220> FEATURE:
<223> OTHER INFORMATION: Sequences to be used as promoter for regulating
      expression of foreign genes

<400> SEQUENCE: 2
ctgtacattc atcttgccgc ctttgcattc acttggccac aaagagtaga gagaaggaag      60
agaagagccc agacttcaag aagcgacctt gcaagtgcac tcgagggtca gaaactgtat     120
atcatatcta tgtgagagaa aggggaacat ttgagatgga gtccatttac ttgaggtata     180
cttattattt tgatcaataa atttgtatac ttcttattta gatcaataaa tttgtcatta     240
agctataatc caaataaat tacgatcaaa tatgcaaatg ttagccagta cttgtgttaa      300
acttgatggc atctcttggt ttctttggca atcacatgcc taagaaataa atagtatcat     360
atgattgtgt ttggtcagac ttcagagtca gatgactctg tttggataaa cagcttaatt     420
aagcgcttat agaatatcat atgattgtgt ttggtcagac ttcagagcat ctcttggttt     480
ctctggcaat catatgccta agaaataaat agtatcatat gattgtgttt ggtcagactt     540
cagagtcaga tgaccctgtt tgggtaaaca gcttaattaa gtgcttatag aataagcgct     600
tatcatataa gtgcttttgt acagttattt ctatgaaagt agaagaaata gtcatattgt     660
tttaatataa gctatcctgg agagcttgtg gaaataacca gaaaagaact tatggacacg     720
tcatgagctg tttacataag atctccctaa cagtctcaaa agtgtttatg ccagtagata     780
aattcaaata agtcaatcta aacagaccct aaatccatta tggtacctat cattttagct     840
tattccatct ttattaagaa tgtcatgaga taacataatg ataacacatt attttgacac     900
aaatgggcag atctagcaat ttaactctgg agtccttcaa gactgctgtt cttacgaagt     960
tcacgtccct gaatcatgtt cctgtatgga agcctgaaag acctcaaatt ctaaaaggtg    1020
gcgataaatt gaaggtttac aaaatatacc ctgcgggctt gacacagagg caagctcttt    1080
ataccttcca gttcaacggg gatgttgatt tcagaagtca cttggagagc aatccttgtg    1140
ccaagtttga agtaattttt gtgtagcata tgttgagcta cctacaattt acatgatcac    1200
ctagcattag ctctttcact taactgagag aatgaagttt taggaatgag tatgaccatg    1260
gagtcggcat ggctttgtaa tgcctaccct actttggcca actcatcggg gatttacatt    1320
cagaaaatat acatgacttc aaccatactt aaacccctttt tgtaagata actgaatgtt    1380 catatttaat gttgggttgt agtgttttta cttgattata tccagacagt tacaagttgg    1440
acaacaagat tgtgggtctg tactgttatt tatttatttt tttttttagca gaaacacctt    1500 atcttttgtt tcgtttgaat gtagaatgaa aataaaagaa agaaaatata acatcatcgg    1560
ccgcgcttgt ctaatttcgg gcagttagga tcctctccgg tcaccggaaa gtttcagtag    1620
aagaaacaaa acaccgtgac taaaatgata ctattatttt atttattgtg tttttctttt    1680
ttctaccgga acttttttaga acggatccca actcgttccg gggccgctac aactgaaaca    1740
aaagaagata ttttctctct cttcagaaat gtaagttttc ctttacagat acccattcac    1800
catttgattc agatgtggtg actagagata aagcatacta atttgactct tggaaaccca    1860
taaagtttat gttatccgtg ttctggacca atccacttgg gggcataacc tgtgtctatg    1920
tgtggtttgg tttccattct gatttatgcg gcgacttgta atttaaaatc taggagggc     1980

-continued

```
agacattgaa caatcccaat attttaataa cttatgcaag attttttttta ttaatgagat    2040 gatgtgtttg tgactgagat tgagtcatac atttcactaa gaaatggttc caagtaccaa    2100
actatcatga cccagttgca acatgacgt tcgggagtgg tcactttgat agttcaattt    2160
catcttggct tcttattcct tttataattc taattcttct tgtgtaaact atttcatgta    2220
ttatttttct ttaaaattta catgtcattt attttgcctc actaactcaa ttttgcatat    2280
aacaatgata agtgatattt tgactcacaa aatttacatc aaatttcgac atcgtttatt    2340
atgttcattg gatgattaac aaatataaca aactttgcaa ctaattaacc accaactgaa    2400
tataattaac tataactgtg aaagtagtta accatattt ttagatgtat atatcatccg     2460
ttgaatgtaa ttattcatat atttgaacta agttacccta caacttaaag aacttaaaga    2520
actcggtttg agacctgggg acgaaaatgt aatgagactt taatgttgac tttgacaccg    2580
caccacatgt gccttttaca tatagtttat atgacaagta atgacaatcc ttgctctatt    2640
ataaggcgac ccttagctcc aaccaaagga cgatggagtt aagaaagaaa ctcttgctta    2700
cttgtaaggt ccacacttct tcactcacct ctcaatttca tcctacaaaa atgtccaaac    2760
ttctctttct cacaatcaca aactcattcc aaacacactc tcttctcc              2808
```

<210> SEQ ID NO 3
<211> LENGTH: 2069
<212> TYPE: DNA
<213> ORGANISM: Artificial Sequence
<220> FEATURE:
<223> OTHER INFORMATION: Sequences to be used as promoter for regulating expression of foreign genes

<400> SEQUENCE: 3

```
gatctcccta acagtctcaa aagtgtttat gccagtagat aaattcaaat aagtcaatct    60
aaacagaccc taaatccatt atggtaccta tcattttagc ttattccatc tttattaaga    120
atgtcatgag ataacataat gataacacat tattttgaca caaatgggca gatctagcaa    180
tttaactctg gagtccttca agactgctgt tcttacgaag ttcacgtccc tgaatcatgt    240
tcctgtatgg aagcctgaaa gacctcaaat tctaaaaggt ggcgataaat tgaaggttta    300
caaaatatac cctgcgggct tgacacagag gcaagctctt tataccttcc agttcaacgg    360
ggatgttgat ttcagaagtc acttggagag caatccttgt gccaagtttg aagtaatttt    420
tgtgtagcat atgttgagct acctacaatt tacatgatca cctagcatta gctctttcac    480
ttaactgaga gaatgaagtt ttaggaatga gtatgaccat ggagtcggca tggctttgta    540
atgcctaccc tactttggcc aactcatcgg ggatttacat tcagaaaata tacatgactt    600
caaccatact taaaccccctt tttgtaagat aactgaatgt tcatatttaa tgttgggttg    660
tagtgttttt acttgattat atccagacag ttacaagttg gacaacaaga ttgtgggtct    720
gtactgttat ttatttattt ttttttagc agaaacacct tatctttttgt ttcgtttgaa    780 tgtagaatga aaataaaaga aagaaaatat aacatcatcg gccgcgcttg tctaatttcg    840
ggcagttagg atcctctccg gtcaccggaa agtttcagta gaagaaacaa acaccgtga    900 ctaaaatgat actattattt tatttattgt gtttttcttt tttctaccgg aacttttag    960 aacggatccc aactcgttcc ggggccgcta caactgaaac aaaagaagat attttctctc    1020
tcttcagaaa tgtaagtttt cctttacaga tacccattca ccatttgatt cagatgtggt    1080
gactagagat aaagcatact aatttgactc ttggaaaccc ataagttta tgttatccgt    1140 gttctggacc aatccacttg ggggcataac ctgtgtctat gtgtggttg gtttccattc    1200
```

```
tgatttatgc ggcgacttgt aatttaaaat ctaggagggg cagacattga acaatcccaa    1260
tattttaata acttatgcaa gattttttt attaatgaga tgatgtgttt gtgactgaga     1320
ttgagtcata catttcacta agaaatggtt ccaagtacca aactatcatg acccagttgc    1380
aaacatgacg ttcgggagtg gtcactttga tagttcaatt tcatcttggc ttcttattcc    1440
ttttataatt ctaattcttc ttgtgtaaac tatttcatgt attattttc tttaaaattt     1500 acatgtcatt tattttgcct cactaactca attttgcata taacaatgat aagtgatatt    1560
ttgactcaca aaatttacat caaatttcga catcgtttat tatgttcatt ggatgattaa    1620
caaatataac aaactttgca actaattaac caccaactga atataattaa ctataactgt    1680
gaaagtagtt aaccatattt tttagatgta tatatcatcc gttgaatgta attattcata    1740
tatttgaact aagttaccct acaacttaaa gaacttaaag aactcggttt gagacctggg    1800
gacgaaaatg taatgagact ttaatgttga ctttgacacc gcaccacatg tgcctttac     1860 atatagttta tatgacaagt aatgacaatc cttgctctat tataaggcga cccttagctc    1920
caaccaaagg acgatggagt taagaaagaa actcttgctt acttgtaagg tccacacttc    1980
ttcactcacc tctcaatttc atcctacaaa aatgtccaaa cttctctttc tcacaatcac    2040
aaactcattc caaacacact ctcttctcc                                      2069
```

<210> SEQ ID NO 4
<211> LENGTH: 1220
<212> TYPE: DNA
<213> ORGANISM: Artificial Sequence
<220> FEATURE:
<223> OTHER INFORMATION: Sequences to be used as promoter for regulating expression of foreign genes

<400> SEQUENCE: 4

```
gatcctctcc ggtcaccgga aagtttcagt agaagaaaca aaacaccgtg actaaaatga      60
tactattatt ttatttattg tgttttttctt ttttctaccg gaactttta gaacggatcc     120 caactcgttc cggggccgct acaactgaaa caaaagaaga tattttctct ctcttcagaa     180
atgtaagttt tccttacag atacccattc accatttgat tcagatgtgg tgactagaga     240
taaagcatac taatttgact cttggaaacc cataaagttt atgttatccg tgttctggac     300
caatccactt gggggcataa cctgtgtcta tgtgtggttt ggtttccatt ctgatttatg     360
cggcgacttg taatttaaaa tctaggaggg gcagacattg aacaatccca atatttaat     420 aacttatgca agatttttt tattaatgag atgatgtgtt tgtgactgag attgagtcat     480
acatttcact aagaaatggt tccaagtacc aaactatcat gacccagttg caaacatgac    540
gttcgggagt ggtcactttg atagttcaat ttcatcttgg cttcttattc cttttataat    600
tctaattctt cttgtgtaaa ctatttcatg tattattttt ctttaaaatt tacatgtcat    660
ttattttgcc tcactaactc aattttgcat ataacaatga taagtgatat tttgactcac    720
aaaatttaca tcaaatttcg acatcgttta ttatgttcat tggatgatta acaaatataa    780
caaactttgc aactaattaa ccaccaactg aatataatta actataactg tgaaagtagt    840
taaccatatt tttagatgt atatatcatc cgttgaatgt aattattcat atatttgaac    900
taagttaccc tacaacttaa agaacttaaa gaactcggtt tgagacctgg ggacgaaaat    960
gtaatgagac tttaatgttg actttgacac cgcaccacat gtgcctttta catatagttt   1020
atatgacaag taatgacaat ccttgctcta ttataaggcg acccttagct ccaaccaaag    1080
gacgatggag ttaagaaaga aactcttgct tacttgtaag gtccacactt cttcactcac    1140
```

-continued

| | |
|---|---|
| ctctcaattt catcctacaa aaatgtccaa acttctcttt ctcacaatca caaactcatt | 1200 |
| ccaaacacac tctcttctcc | 1220 |

<210> SEQ ID NO 5
<211> LENGTH: 2863
<212> TYPE: DNA
<213> ORGANISM: Artificial Sequence
<220> FEATURE:
<223> OTHER INFORMATION: Sequences to be used as promoter for regulating
      expression of foreign genes

<400> SEQUENCE: 5

| | |
|---|---|
| ctgtacattc atcttgccgc ctttgcattc acttggccac aaagagtaga gagaaggaag | 60 |
| agaagagccc agacttcaag aagcgacctt gcaagtgcac tcgagggtca gaactgtat | 120 |
| atcatatcta tgtgagagaa agggaacat ttgagatgga gtccatttac ttgaggtata | 180 |
| cttattattt tgatcaataa atttgtatac ttcttattta gatcaataaa tttgtcatta | 240 |
| agctataatc caaataaat tacgatcaaa tatgcaaatg ttagccagta cttgtgttaa | 300 |
| acttgatggc atctcttggt ttctttggca atcacatgcc taagaaataa atagtatcat | 360 |
| atgattgtgt ttggtcagac ttcagagtca gatgactctg tttggataaa cagcttaatt | 420 |
| aagcgcttat agaatatcat atgattgtgt ttggtcagac ttcagagcat ctcttggttt | 480 |
| ctctggcaat catatgccta agaaataaat agtatcatat gattgtgttt ggtcagactt | 540 |
| cagagtcaga tgaccctgtt tgggtaaaca gcttaattaa gtgcttatag aataagcgct | 600 |
| tatcatataa gtgcttttgt acagttattt ctatgaaagt agaagaaata gtcatattgt | 660 |
| tttaatataa gctatcctgg agagcttgtg gaaataacca gaaagaact tatggacacg | 720 |
| tcatgagctg tttacataag atctccctaa cagtctcaaa agtgtttatg ccagtagata | 780 |
| aattcaaata agtcaatcta aacagaccct aaatccatta tggtacctat cattttagct | 840 |
| tattccatct ttattaagaa tgtcatgaga taacataatg ataacacatt attttgacac | 900 |
| aaatgggcag atctagcaat ttaactctgg agtccttcaa gactgctgtt cttacgaagt | 960 |
| tcacgtccct gaatcatgtt cctgtatgga agcctgaaag acctcaaatt ctaaaaggtg | 1020 |
| gcgataaatt gaaggtttac aaaatatacc ctgcgggctt gacacagagg caagctcttt | 1080 |
| ataccttcca gttcaacggg gatgttgatt tcagaagtca cttggagagc aatccttgtg | 1140 |
| ccaagtttga agtaattttt gtgtagcata tgttgagcta cctacaattt acatgatcac | 1200 |
| ctagcattag ctctttcact taactgagag aatgaagttt taggaatgag tatgaccatg | 1260 |
| gagtcggcat ggctttgtaa tgcctaccct actttggcca actcatcggg gatttacatt | 1320 |
| cagaaaatat acatgacttc aaccatactt aaacccctt ttgtaagata actgaatgtt | 1380 |
| catatttaat gttgggttgt agtgttttta cttgattata ccagacagt tacaagttgg | 1440 |
| acaacaagat tgtgggtctg tactgttatt tatttatttt tttttagca gaaacacctt | 1500 |
| atcttttgtt tcgtttgaat gtagaatgaa aataaagaa agaaaatata acatcatcgg | 1560 |
| ccgcgcttgt ctaatttcgg gcagttagga tcctctccgg tcaccggaaa gtttcagtag | 1620 |
| aagaaacaaa acaccgtgac taaaatgata ctattatttt atttattgtg tttttctttt | 1680 |
| ttctaccgga actttttaga acggatccca actcgttccg gggccgctac aactgaaaca | 1740 |
| aaagaagata ttttctctct cttcagaaat gtaagttttc ctttacagat acccattcac | 1800 |
| catttgattc agatgtggtg actagagata aagcatacta atttgactct tggaaaccca | 1860 |
| taaagtttat gttatccgtg ttctggacca atccacttgg gggcataacc tgtgtctatg | 1920 |

-continued

```
tgtggtttgg tttccattct gatttatgcg gcgacttgta atttaaaatc taggagggc    1980 agacattgaa caatcccaat attttaataa cttatgcaag atttttttta ttaatgagat    2040
gatgtgtttg tgactgagat tgagtcatac atttcactaa gaaatggttc caagtaccaa    2100
actatcatga cccagttgca acatgacgt tcgggagtgg tcactttgat agttcaattt    2160
catcttggct tcttattcct tttataattc taattcttct tgtgtaaact atttcatgta    2220
ttatttttct ttaaaattta catgtcattt attttgcctc actaactcaa ttttgcatat    2280
aacaatgata agtgatattt tgactcacaa aatttacatc aaatttcgac atcgtttatt    2340
atgttcattg gatgattaac aaatataaca aactttgcaa ctaattaacc accaactgaa    2400
tataattaac tataactgtg aaagtagtta accatatttt ttagatgtat atatcatccg    2460
ttgaatgtaa ttattcatat atttgaacta agttacccta caacttaaag aacttaaaga    2520 actcggttg agacctgggg acgaaaatgt aatgagactt taatgttgac tttgacaccg    2580
caccacatgt gcctttaca tatagtttat atgacaagta atgacaatcc ttgctctatt    2640
ataaggcgac cctagctcc aaccaaagga cgatggagtt aagaaagaaa ctcttgctta    2700
cttgtaaggt ccacacttct tcactcacct ctcaatttca tcctacaaaa atgtccaaac    2760
ttctctttct cacaatcaca aactcattcc aaacacactc tcttctccaa aaatgtcttc    2820
cttctcagta cgtttcctca ccccaccatc catctctcgt ccc                     2863
```

<210> SEQ ID NO 6
<211> LENGTH: 2124
<212> TYPE: DNA
<213> ORGANISM: Artificial Sequence
<220> FEATURE:
<223> OTHER INFORMATION: Sequences to be used as promoter for regulating expression of foreign genes

<400> SEQUENCE: 6

```
gatctcccta acagtctcaa aagtgtttat gccagtagat aaattcaaat aagtcaatct      60
aaacagaccc taaatccatt atggtaccta tcattttagc ttattccatc tttattaaga    120
atgtcatgag ataacataat gataacacat tattttgaca caaatgggca gatctagcaa    180
tttaactctg gagtccttca agactgctgt tcttacgaag ttcacgtccc tgaatcatgt    240
tcctgtatgg aagcctgaaa gacctcaaat tctaaaaggt ggcgataaat tgaaggttta    300
caaaatatac cctgcgggct tgacacagag gcaagctctt tataccttcc agttcaacgg    360
ggatgttgat ttcagaagtc acttggagag caatccttgt gccaagtttg aagtaatttt    420
tgtgtagcat atgttgagct acctacaatt tacatgatca cctagcatta gctctttcac    480
ttaactgaga gaatgaagtt ttaggaatga gtatgaccat ggagtcggca tggctttgta    540
atgcctaccc tactttggcc aactcatcgg ggatttacat tcagaaaata tacatgactt    600
caaccatact taaacccctt tttgtaagat aactgaatgt tcatatttaa tgttgggttg    660
tagtgttttt acttgattat atccagacag ttacaagttg gacaacaaga ttgtgggtct    720
gtactgttat ttatttattt tttttttagc agaaacacct tatctttgt ttcgtttgaa    780 tgtagaatga aaataaaaga aagaaaatat aacatcatcg gccgcgcttg tctaatttcg    840
ggcagttagg atcctctccg gtcaccggaa agtttcagta gaagaaacaa acaccgtga    900 ctaaaatgat actattattt tatttattgt gttttctttt tttctaccgg aactttttag    960
aacggatccc aactcgttcc ggggccgcta caactgaaac aaaagaagat attttctctc   1020
tcttcagaaa tgtaagttttt cctttacaga tacccattca ccatttgatt cagatgtggt   1080
```

-continued

```
gactagagat aaagcatact aatttgactc ttggaaaccc ataaagttta tgttatccgt    1140
gttctggacc aatccacttg ggggcataac ctgtgtctat gtgtggtttg gtttccattc    1200
tgatttatgc ggcgacttgt aatttaaaat ctaggagggg cagacattga acaatcccaa    1260
tattttaata acttatgcaa gattttttt attaatgaga tgatgtgttt gtgactgaga     1320
ttgagtcata catttcacta agaaatggtt ccaagtacca aactatcatg acccagttgc    1380
aaacatgacg ttcgggagtg gtcactttga tagttcaatt tcatcttggc ttcttattcc    1440
ttttataatt ctaattcttc ttgtgtaaac tatttcatgt attattttc tttaaaattt     1500 acatgtcatt tattttgcct cactaactca attttgcata taacaatgat aagtgatatt    1560
ttgactcaca aaatttacat caaatttcga catcgtttat tatgttcatt ggatgattaa    1620
caaatataac aaactttgca actaattaac caccaactga atataattaa ctataactgt    1680
gaaagtagtt aaccatattt tttagatgta tatatcatcc gttgaatgta attattcata    1740
tatttgaact aagttaccct acaacttaaa gaacttaaag aactcggttt gagacctggg    1800
gacgaaaatg taatgagact ttaatgttga cttttgacacc gcaccacatg tgccttttac    1860
atatagttta tatgacaagt aatgacaatc cttgctctat tataaggcga cccttagctc    1920
caaccaaagg acgatggagt taagaaagaa actcttgctt acttgtaagg tccacacttc    1980
ttcactcacc tctcaatttc atcctacaaa aatgtccaaa cttctctttc tcacaatcac    2040
aaactcattc caaacacact ctcttctcca aaaatgtctt ccttctcagt acgtttcctc    2100
accccaccat ccatctctcg tccc                                          2124
```

<210> SEQ ID NO 7
<211> LENGTH: 1160
<212> TYPE: DNA
<213> ORGANISM: Artificial Sequence
<220> FEATURE:
<223> OTHER INFORMATION: Sequences to be used as promoter for regulating
      expression of foreign genes

<400> SEQUENCE: 7

```
gatcccaact cgttccgggg ccgctacaac tgaaacaaaa gaagatattt tctctctctt      60
cagaaatgta agttttcctt tacagatacc cattccaccat ttgattcaga tgtggtgact    120
agagataaag catactaatt tgactcttgg aaacccataa agtttatgtt atccgtgttc     180
tggaccaatc cacttggggg cataacctgt gtctatgtgt ggtttggttt ccattctgat    240
ttatgcggcg acttgtaatt taaaatctag gaggggcaga cattgaacaa tcccaatatt    300
ttaataactt atgcaagatt ttttttatta atgagatgat gtgttgtga ctgagattga     360 gtcatacatt tcactaagaa atggttccaa gtaccaaact atcatgaccc agttgcaaac    420
atgacgttcg ggagtggtca ctttgatagt tcaatttcat cttggcttct tattcctttt    480
ataattctaa ttcttcttgt gtaaactatt tcatgtatta ttttctttta aaatttacat    540
gtcatttatt ttgcctcact aactcaattt tgcatataac aatgataagt gatattttga    600
ctcacaaaat ttacatcaaa tttcgacatc gtttattatg ttcattggat gattaacaaa    660
tataacaaac tttgcaacta attaaccacc aactgaatat aattaactat aactgtgaaa    720
gtagttaacc atatttttta gatgtatata tcatccgttg aatgtaatta ttcatatatt    780
tgaactaagt taccctacaa cttaaagaac ttaagaact cggtttgaga cctggggacg    840
aaaatgtaat gagactttaa tgttgacttt gacaccgcac cacatgtgcc ttttacatat    900
agtttatatg acaagtaatg acaatccttg ctctattata aggcgaccct tagctccaac    960
```

-continued

| | |
|---|---|
| caaaggacga tggagttaag aaagaaactc ttgcttactt gtaaggtcca cacttcttca | 1020 |
| ctcacctctc aatttcatcc tacaaaaatg tccaaacttc tctttctcac aatcacaaac | 1080 |
| tcattccaaa cacactctct tctccaaaaa tgtcttcctt ctcagtacgt ttcctcaccc | 1140 |
| caccatccat ctctcgtccc | 1160 |

<210> SEQ ID NO 8
<211> LENGTH: 2904
<212> TYPE: DNA
<213> ORGANISM: Artificial Sequence
<220> FEATURE:
<223> OTHER INFORMATION: Sequences to be used as promoter for regulating expression of foreign genes

<400> SEQUENCE: 8

| | |
|---|---|
| ctgtacattc atcttgccgc ctttgcattc acttggccac aaagagtaga gagaaggaag | 60 |
| agaagagccc agacttcaag aagcgacctt gcaagtgcac tcgagggtca gaaactgtat | 120 |
| atcatatcta tgtgagagaa agggaacat ttgagatgga gtccatttac ttgaggtata | 180 |
| cttattattt tgatcaataa atttgtatac ttcttattta gatcaataaa tttgtcatta | 240 |
| agctataatc caaaataaat tacgatcaaa tatgcaaatg ttagccagta cttgtgttaa | 300 |
| acttgatggc atctcttggt ttctttggca atcacatgcc taagaaataa atagtatcat | 360 |
| atgattgtgt ttggtcagac ttcagagtca gatgactctg tttggataaa cagcttaatt | 420 |
| aagcgcttat agaatatcat atgattgtgt ttggtcagac ttcagagcat ctcttggttt | 480 |
| ctctggcaat catatgccta agaaataaat agtatcatat gattgtgttt ggtcagactt | 540 |
| cagagtcaga tgaccctgtt tgggtaaaca gcttaattaa gtgcttatag aataagcgct | 600 |
| tatcatataa gtgcttttgt acagttattt ctatgaaagt agaagaaata gtcatattgt | 660 |
| tttaatataa gctatcctgg agagcttgtg gaaataacca gaaagaact tatggacacg | 720 |
| tcatgagctg tttacataag atctccctaa cagtctcaaa agtgtttatg ccagtagata | 780 |
| aattcaaata agtcaatcta aacagaccct aaatccatta tggtacctat cattttagct | 840 |
| tattccatct ttattaagaa tgtcatgaga taacataatg ataacacatt attttgacac | 900 |
| aaatgggcag atctagcaat ttaactctgg agtccttcaa gactgctgtt cttacgaagt | 960 |
| tcacgtccct gaatcatgtt cctgtatgga agcctgaaag acctcaaatt ctaaaaggtg | 1020 |
| gcgataaatt gaaggtttac aaaatatacc ctgcgggctt gacacagagg caagctcttt | 1080 |
| ataccttcca gttcaacggg gatgttgatt tcagaagtca cttggagagc aatccttgtg | 1140 |
| ccaagtttga agtaattttt gtgtagcata tgttgagcta cctacaattt acatgatcac | 1200 |
| ctagcattag ctctttcact taactgagag aatgaagttt taggaatgag tatgaccatg | 1260 |
| gagtcggcat ggctttgtaa tgcctaccct actttggcca actcatcggg gatttacatt | 1320 |
| cagaaaatat acatgacttc aaccatactt aaaccccttt ttgtaagata actgaatgtt | 1380 |
| catatttaat gttgggttgt agtgttttta cttgattata ccagacagt tacaagttgg | 1440 |
| acaacaagat tgtgggtctg tactgttatt tatttatttt tttttagca gaaacacctt | 1500 |
| atcttttgtt tcgtttgaat gtagaatgaa aataaaagaa agaaaatata acatcatcgg | 1560 |
| ccgcgcttgt ctaatttcgg gcagttagga tcctctccgg tcaccggaaa gtttcagtag | 1620 |
| aagaaacaaa acaccgtgac taaaatgata ctattatttt atttattgtg tttttctttt | 1680 |
| ttctaccgga acttttttaga acggatccca actcgttccg gggccgctac aactgaaaca | 1740 |
| aaagaagata ttttctctct cttcagaaat gtaagttttc ctttacagat acccattcac | 1800 |

-continued

```
catttgattc agatgtggtg actagagata aagcatacta atttgactct tggaaaccca    1860
taaagtttat gttatccgtg ttctggacca atccacttgg gggcataacc tgtgtctatg    1920
tgtggtttgg tttccattct gatttatgcg gcgacttgta atttaaaatc taggaggggc    1980
agacattgaa caatcccaat attttaataa cttatgcaag attttttttta ttaatgagat    2040 gatgtgtttg tgactgagat tgagtcatac atttcactaa gaaatggttc caagtaccaa    2100
actatcatga cccagttgca aacatgacgt tcgggagtgg tcactttgat agttcaattt    2160
catcttggct tcttattcct tttataattc taattcttct tgtgtaaact atttcatgta    2220 ttattttttct ttaaaatttta catgtcattt attttgcctc actaactcaa ttttgcatat    2280
aacaatgata agtgatattt tgactcacaa aatttacatc aaatttcgac atcgtttatt    2340
atgttcattg gatgattaac aaatataaca aactttgcaa ctaattaacc accaactgaa    2400
tataattaac tataactgtg aaagtagtta accatatttt ttagatgtat atatcatccg    2460
ttgaatgtaa ttattcatat atttgaacta agttacccta caacttaaag aacttaaaga    2520
actcggtttg agacctgggg acgaaaatgt aatgagactt taatgttgac tttgacaccg    2580
caccacatgt gccttttaca tatagtttat atgacaagta atgacaatcc ttgctctatt    2640
ataaggcgac ccttagctcc aaccaaagga cgatggagtt aagaaagaaa ctcttgctta    2700
cttgtaaggt ccacacttct tcactcacct ctcaatttca tcctacaaaa atgtccaaac    2760
ttctctttct cacaatcaca aactcattcc aaacacactc tcttctccaa aaatgtcttc    2820
cttctcagta cgtttcctca ccccaccatc catctctcgt cccaacaaaa catggctact    2880
atctgctgca actccatcag ttgc                                            2904
```

<210> SEQ ID NO 9
<211> LENGTH: 2165
<212> TYPE: DNA
<213> ORGANISM: Artificial Sequence
<220> FEATURE:
<223> OTHER INFORMATION: Sequences to be used as promoter for regulating expression of foreign genes

<400> SEQUENCE: 9

```
gatctcccta acagtctcaa aagtgtttat gccagtagat aaattcaaat aagtcaatct     60
aaacagaccc taaatccatt atggtaccta tcattttagc ttattccatc tttattaaga    120
atgtcatgag ataacataat gataacacat tattttgaca caaatgggca gatctagcaa    180
tttaactctg gagtccttca agactgctgt tcttacgaag ttcacgtccc tgaatcatgt    240
tcctgtatgg aagcctgaaa gacctcaaat tctaaaaggt ggcgataaat tgaaggttta    300
caaaatatac cctgcgggct tgacacagag gcaagctctt tataccttcc agttcaacgg    360
ggatgttgat ttcagaagtc acttggagag caatccttgt gccaagtttg aagtaatttt    420
tgtgtagcat atgttgagct acctacaatt tacatgatca cctagcatta gctctttcac    480
ttaactgaga gaatgaagtt ttaggaatga gtatgaccat ggagtcggca tggctttgta    540
atgcctaccc tactttggcc aactcatcgg ggatttacat tcagaaaata tacatgactt    600
caaccatact taaaccccctt tttgtaagat aactgaatgt tcatatttaa tgttgggttg    660
tagtgttttt acttgattat atccagacag ttacaagttg gacaacaaga ttgtgggtct    720
gtactgttat ttatttattt tttttttagc agaaacacct tatcttttgt ttcgtttgaa    780
tgtagaatga aaataaaaga aagaaatat aacatcatcg gccgcgcttg tctaatttcg    840
ggcagttagg atcctctccg gtcaccggaa agtttcagta gaagaaacaa acaccgtga    900
```

```
ctaaaatgat actattattt tatttattgt gttttctttt tttctaccgg aacttttag        960
aacggatccc aactcgttcc ggggccgcta caactgaaac aaaagaagat attttctctc       1020
tcttcagaaa tgtaagtttt cctttacaga tacccattca ccatttgatt cagatgtggt       1080
gactagagat aaagcatact aatttgactc ttggaaaccc ataaagttta tgttatccgt       1140
gttctggacc aatccacttg ggggcataac ctgtgtctat gtgtggtttg gtttccattc       1200
tgatttatgc ggcgacttgt aatttaaaat ctaggagggg cagacattga acaatcccaa       1260
tattttaata acttatgcaa gattttttt attaatgaga tgatgtgttt gtgactgaga        1320
ttgagtcata catttcacta agaaatggtt ccaagtacca aactatcatg acccagttgc       1380
aaacatgacg ttcgggagtg gtcactttga tagttcaatt tcatcttggc ttcttattcc       1440
ttttataatt ctaattcttc ttgtgtaaac tatttcatgt attattttc tttaaaattt        1500
acatgtcatt tattttgcct cactaactca attttgcata taacaatgat aagtgatatt       1560
ttgactcaca aaatttacat caaatttcga catcgtttat tatgttcatt ggatgattaa       1620
caaatataac aaactttgca actaattaac caccaactga atataattaa ctataactgt       1680
gaaagtagtt aaccatattt tttagatgta tatatcatcc gttgaatgta attattcata       1740
tatttgaact aagttaccct acaacttaaa gaacttaaag aactcggttt gagacctggg       1800
gacgaaaatg taatgagact ttaatgttga ctttgacacc gcaccacatg tgccttttac       1860
atatagttta tatgacaagt aatgacaatc cttgctctat tataaggcga cccttagctc       1920
caaccaaagg acgatggagt taagaaagaa actcttgctt acttgtaagg tccacacttc       1980
ttcactcacc tctcaatttc atcctacaaa aatgtccaaa cttctctttc tcacaatcac       2040
aaactcattc caaacacact ctcttctcca aaaatgtctt ccttctcagt acgtttcctc       2100
accccaccat ccatctctcg tcccaacaaa acatggctac tatctgctgc aactccatca       2160
gttgc                                                                   2165

<210> SEQ ID NO 10
<211> LENGTH: 1316
<212> TYPE: DNA
<213> ORGANISM: Artificial Sequence
<220> FEATURE:
<223> OTHER INFORMATION: Sequences to be used as promoter for regulating
      expression of foreign genes

<400> SEQUENCE: 10
gatcctctcc ggtcaccgga agtttcagt agaagaaaca aaacaccgtg actaaaatga        60
tactattatt ttatttattg tgttttctt ttttctaccg aacttttta gaacggatcc        120
caactcgttc cggggccgct acaactgaaa caaaagaaga tattttctct ctcttcagaa       180
atgtaagttt cctttacag atacccattc accatttgat tcagatgtgg tgactagaga       240
taaagcatac taatttgact cttggaaacc cataaagttt atgttatccg tgttctggac       300
caatccactt ggggcataa cctgtgtcta tgtgtggttt ggtttccatt ctgatttatg        360
cggcgacttg taatttaaaa tctaggaggg gcagacattg aacaatccca atatttaat        420
aacttatgca agattttttt tattaatgag atgatgtgtt tgtgactgag attgagtcat       480
acatttcact aagaaatggt tccaagtacc aaactatcat gacccagttg caaacatgac       540
gttcgggagt ggtcactttg atagttcaat tcatcttgg cttcttattc cttttataat        600
tctaattctt cttgtgtaaa ctatttcatg tattattttt cttaaaatt tacatgtcat       660
ttattttgcc tcactaactc aattttgcat ataacaatga taagtgatat tttgactcac       720
```

-continued

| | |
|---|---|
| aaaatttaca tcaaatttcg acatcgttta ttatgttcat tggatgatta acaaatataa | 780 |
| caaactttgc aactaattaa ccaccaactg aatataatta actataactg tgaaagtagt | 840 |
| taaccatatt ttttagatgt atatatcatc cgttgaatgt aattattcat atatttgaac | 900 |
| taagttaccc tacaacttaa agaacttaaa gaactcggtt tgagacctgg ggacgaaaat | 960 |
| gtaatgagac tttaatgttg actttgacac cgcaccacat gtgccttta catatagttt | 1020 |
| atatgacaag taatgacaat ccttgctcta ttataaggcg acccttagct ccaaccaaag | 1080 |
| gacgatggag ttaagaaaga aactcttgct tacttgtaag gtccacactt cttcactcac | 1140 |
| ctctcaattt catcctacaa aaatgtccaa acttctcttt ctcacaatca caaactcatt | 1200 |
| ccaaacacac tctcttctcc aaaaatgtct tccttctcag tacgtttcct caccccacca | 1260 |
| tccatctctc gtcccaacaa aacatggcta ctatctgctg caactccatc agttgc | 1316 |

<210> SEQ ID NO 11
<211> LENGTH: 2971
<212> TYPE: DNA
<213> ORGANISM: Artificial Sequence
<220> FEATURE:
<223> OTHER INFORMATION: Sequences to be used as promoter for regulating
    expression of foreign genes

<400> SEQUENCE: 11

| | |
|---|---|
| ctgtacattc atcttgccgc ctttgcattc acttggccac aaagagtaga gagaaggaag | 60 |
| agaagagccc agacttcaag aagcgacctt gcaagtgcac tcgagggtca gaaactgtat | 120 |
| atcatatcta tgtgagagaa agggaacat ttgagatgga gtccatttac ttgaggtata | 180 |
| cttattattt tgatcaataa atttgtatac ttcttattta gatcaataaa tttgtcatta | 240 |
| agctataatc caaaataaat tacgatcaaa tatgcaaatg ttagccagta cttgtgttaa | 300 |
| acttgatggc atctcttggt ttctttggca atcacatgcc taagaaataa atagtatcat | 360 |
| atgattgtgt ttggtcagac ttcagagtca gatgactctg tttggataaa cagcttaatt | 420 |
| aagcgcttat agaatatcat atgattgtgt ttggtcagac ttcagagcat ctcttggttt | 480 |
| ctctggcaat catatgccta agaaataaat agtatcatat gattgtgttt ggtcagactt | 540 |
| cagagtcaga tgaccctgtt tgggtaaaca gcttaattaa gtgcttatag aataagcgct | 600 |
| tatcatataa gtgcttttgt acagttattt ctatgaaagt agaagaaata gtcatattgt | 660 |
| tttaatataa gctatcctgg agagcttgtg gaaataacca gaaaagaact tatggacacg | 720 |
| tcatgagctg tttacataag atctccctaa cagtctcaaa agtgtttatg ccagtagata | 780 |
| aattcaaata agtcaatcta aacagaccct aaatccatta tggtacctat cattttagct | 840 |
| tattccatct ttattaagaa tgtcatgaga taacataatg ataacacatt atttgacac | 900 |
| aaatgggcag atctagcaat ttaactctgg agtccttcaa gactgctgtt cttacgaagt | 960 |
| tcacgtccct gaatcatgtt cctgtatgga agcctgaaaa acctcaaatt ctaaaaggtg | 1020 |
| gcgataaatt gaaggtttac aaaatatacc ctgcgggctt gacacagagg caagctcttt | 1080 |
| ataccttcca gttcaacggg gatgttgatt tcagaagtca cttggagagc aatccttgtg | 1140 |
| ccaagtttga agtaattttt gtgtagcata tgttgagcta cctacaattt acatgatcac | 1200 |
| ctagcattag ctcttttcact taactgagag aatgaagttt taggaatgag tatgaccatg | 1260 |
| gagtcggcat ggctttgtaa tgcctaccct actttggcca actcatcggg gatttacatt | 1320 |
| cagaaaatat acatgacttc aaccatactt aaaccccttt ttgtaagata actgaatgtt | 1380 |
| catatttaat gttgggttgt agtgttttta cttgattata tccagacagt tacaagttgg | 1440 |

-continued

```
acaacaagat tgtgggtctg tactgttatt tatttatttt tttttttagca gaaacacctt    1500 atcttttgtt tcgtttgaat gtagaatgaa aataaaagaa agaaaatata acatcatcgg    1560
ccgcgcttgt ctaatttcgg gcagttagga tcctctccgg tcaccggaaa gtttcagtag    1620
aagaaacaaa acaccgtgac taaaatgata ctattatttt atttattgtg ttttttcttttt  1680 ttctaccgga acttttagga acggatccca actcgttccg gggccgctac aactgaaaca    1740
aaagaagata ttttctctct cttcagaaat gtaagttttc ctttacagat acccattcac    1800
catttgattc agatgtggtg actagagata aagcatacta atttgactct tggaaaccca    1860
taaagtttat gttatccgtg ttctggacca atccacttgg gggcataacc tgtgtctatg    1920
tgtggtttgg tttccattct gatttatgcg gcgacttgta atttaaaatc taggaggggc    1980
agacattgaa caatcccaat atttttaataa cttatgcaag attttttttta ttaatgagat   2040 gatgtgtttg tgactgagat tgagtcatac atttcactaa gaaatggttc caagtaccaa    2100
actatcatga cccagttgca aacatgacgt tcgggagtgg tcactttgat agttcaattt    2160
catcttggct tcttattcct tttataattc taattcttct tgtgtaaact atttcatgta    2220
ttatttttct ttaaaattta catgtcattt attttgcctc actaactcaa ttttgcatat    2280
aacaatgata agtgatattt tgactcacaa aatttacatc aaatttcgac atcgtttatt    2340
atgttcattg gatgattaac aaatataaca aactttgcaa ctaattaacc accaactgaa    2400
tataattaac tataactgtg aaagtagtta accatattttt ttagatgtat atatcatccg   2460
ttgaatgtaa ttattcatat atttgaacta agttaccctta caacttaaag aacttaaaga   2520
actcggtttg agacctgggg acgaaaatgt aatgagactt taatgttgac tttgacaccg    2580
caccacatgt gccttttaca tatagtttat atgacaagta atgacaatcc ttgctctatt    2640
ataaggcgac ccttagctcc aaccaaagga cgatggagtt aagaaagaaa ctcttgctta    2700
cttgtaaggt ccacacttct tcactcacct ctcaatttca tcctacaaaa atgtccaaac    2760
ttctctttct cacaatcaca aactcattcc aaacacactc tcttctccaa aaatgtcttc    2820
cttctcagta cgtttcctca ccccaccatc catctctcgt cccaacaaaa catggctact    2880
atctgctgca actccatcag ttgcacctgt ttcaacacca caagttgatg catcaaggtt    2940
ggagcctaga gttgaggaaa aagatggtta c                                   2971
```

<210> SEQ ID NO 12
<211> LENGTH: 2232
<212> TYPE: DNA
<213> ORGANISM: Artificial Sequence
<220> FEATURE:
<223> OTHER INFORMATION: Sequences to be used as promoter for regulating expression of foreign genes

<400> SEQUENCE: 12

```
gatctcccta acagtctcaa aagtgtttat gccagtagat aaattcaaat aagtcaatct      60
aaacagaccc taaatccatt atggtaccta tcatttttagc ttattccatc tttattaaga   120
atgtcatgag ataacataat gataacacat tattttgaca caaatgggca gatctagcaa    180
tttaactctg gagtccttca agactgctgt tcttacgaag ttcacgtccc tgaatcatgt    240
tcctgtatgg aagcctgaaa gacctcaaat tctaaaaggt ggcgataaat tgaaggttta    300
caaaatatac cctgcgggct tgacacagag gcaagctctt tataccttcc agttcaacgg    360
ggatgttgat ttcagaagtc acttggagag caatccttgt gccaagtttg aagtaatttta   420 tgtgtagcat atgttgagct acctacaatt tacatgatca cctagcatta gctctttcac    480
```

-continued

```
ttaactgaga gaatgaagtt ttaggaatga gtatgaccat ggagtcggca tggctttgta      540
atgcctaccc tactttggcc aactcatcgg ggatttacat tcagaaaata tacatgactt      600
caaccatact taaacccctt tttgtaagat aactgaatgt tcatatttaa tgttgggttg      660
tagtgttttt acttgattat atccagacag ttacaagttg acaacaaga ttgtgggtct       720 gtactgttat ttatttattt tttttttagc agaaacacct tatcttttgt ttcgtttgaa      780
tgtagaatga aaataaaaga aagaaaatat aacatcatcg gccgcgcttg tctaatttcg      840
ggcagttagg atcctctccg gtcaccggaa agtttcagta aagaaacaa acaccgtga        900 ctaaaatgat actattattt tatttattgt gttttcttt tttctaccgg aactttttag       960
aacggatccc aactcgttcc ggggccgcta caactgaaac aaaagaagat attttctctc     1020
tcttcagaaa tgtaagtttt ccttacaga tacccattca ccatttgatt cagatgtggt      1080
gactagagat aaagcatact aatttgactc ttggaaaccc ataaagttta tgttatccgt     1140
gttctggacc aatccacttg ggggcataac ctgtgtctat gtgtggtttg gtttccattc     1200
tgatttatgc ggcgacttgt aatttaaaat ctaggagggg cagacattga acaatcccaa     1260
tattttaata acttatgcaa gattttttt attaatgaga tgatgtgttt gtgactgaga       1320
ttgagtcata catttcacta agaaatggtt ccaagtacca aactatcatg acccagttgc     1380
aaacatgacg ttcgggagtg gtcactttga tagttcaatt tcatcttggc ttcttattcc     1440
ttttataatt ctaattcttc ttgtgtaaac tatttcatgt attattttc tttaaaattt      1500 acatgtcatt tattttgcct cactaactca attttgcata taacaatgat aagtgatatt     1560
ttgactcaca aaatttacat caaatttcga catcgtttat tatgttcatt ggatgattaa     1620
caaatataac aaactttgca actaattaac caccaactga atataattaa ctataactgt     1680
gaaagtagtt aaccatattt tttagatgta tatatcatcc gttgaatgta attattcata     1740
tatttgaact aagttaccct acaacttaaa gaacttaaag aactcggttt gagacctggg     1800
gacgaaaatg taatgagact ttaatgttga ctttgacacc gcaccacatg tgcctttac     1860 atatagttta tatgacaagt aatgacaatc cttgctctat tataaggcga cccttagctc     1920
caaccaaagg acgatggagt taagaaagaa actcttgctt acttgtaagg tccacacttc     1980
ttcactcacc tctcaatttc atcctacaaa aatgtccaaa cttctctttc tcacaatcac     2040
aaactcattc caaacacact ctcttctcca aaaatgtctt ccttctcagt acgtttcctc     2100
accccaccat ccatctctcg tcccaacaaa acatggctac tatctgctgc aactccatca     2160
gttgcacctg tttcaacacc acaagttgat gcatcaaggt tggagcctag agttgaggaa     2220
aaagatggtt ac                                                        2232
```

<210> SEQ ID NO 13
<211> LENGTH: 1383
<212> TYPE: DNA
<213> ORGANISM: Artificial Sequence
<220> FEATURE:
<223> OTHER INFORMATION: Sequences to be used as promoter for regulating
      expression of foreign genes

<400> SEQUENCE: 13

```
gatcctctcc ggtcaccgga aagtttcagt agaagaaaca aaacaccgtg actaaaatga       60
tactattatt ttatttattg tgttttctt ttttctaccg gaacttttta gaacggatcc      120
caactcgttc cggggccgct acaactgaaa caaaagaaga tattttctct ctcttcagaa     180
atgtaagttt cccttacag atacccattc accatttgat tcagatgtgg tgactagaga      240
```

-continued

```
taaagcatac taatttgact cttggaaacc cataaagttt atgttatccg tgttctggac      300
caatccactt gggggcataa cctgtgtcta tgtgtggttt ggtttccatt ctgatttatg      360
cggcgacttg taatttaaaa tctaggaggg gcagacattg aacaatccca atattttaat      420
aacttatgca agatttttt tattaatgag atgatgtgtt tgtgactgag attgagtcat       480
acatttcact aagaaatggt tccaagtacc aaactatcat gacccagttg caaacatgac     540
gttcgggagt ggtcactttg atagttcaat ttcatcttgg cttcttattc cttttataat     600
tctaattctt cttgtgtaaa ctatttcatg tattattttt cttaaaatt tacatgtcat      660 ttattttgcc tcactaactc aattttgcat ataacaatga taagtgatat tttgactcac    720
aaaatttaca tcaaatttcg acatcgttta ttatgttcat tggatgatta acaaatataa   780
caaactttgc aactaattaa ccaccaactg aatataatta actataactg tgaaagtagt  840
taaccatatt ttttagatgt atatatcatc cgttgaatgt aattattcat atatttgaac  900
taagttaccc tacaacttaa agaacttaaa gaactcggtt tgagacctgg ggacgaaaat  960
gtaatgagac tttaatgttg actttgacac cgcaccacat gtgccttta catatagttt    1020 atatgacaag taatgacaat ccttgctcta ttataaggcg acccttagct ccaaccaaag  1080
gacgatggag ttaagaaaga aactcttgct tacttgtaag gtccacactt cttcactcac  1140
ctctcaattt catcctacaa aaatgtccaa acttctcttt ctcacaatca caaactcatt  1200
ccaaacacac tctcttctcc aaaaatgtct tccttctcag tacgtttcct caccccacca   1260
tccatctctc gtcccaacaa acatggcta ctatctgctg caactccatc agttgcacct    1320
gtttcaacac cacaagttga tgcatcaagg ttggagccta gagttgagga aaagatggt   1380 tac                                                                  1383
```

<210> SEQ ID NO 14
<211> LENGTH: 3472
<212> TYPE: DNA
<213> ORGANISM: Artificial Sequence
<220> FEATURE:
<223> OTHER INFORMATION: Sequences to be used as terminator for regulating expression of foreign genes

<400> SEQUENCE: 14

```
caagttgatg catcaaggtt ggagcctaga gttgaggaaa aagatggtta ctgggtttg      60 aaggaagagt atagaggagg tattaatcct caggagaaag ttaagattca gaaagaacct   120
atgaagcttt ttatggaagg tgggattaat gatttggcta atatgtctct tgaagagatt   180
gaaagctcta agcttactaa agatgatatt gatgttagac ttaaatggct tggtcttttt   240
catagaagga aacatcattg taagtttttt tactttcttt ttatacttca aagttctctc   300
atactctgta tttgttttatt agttttttgta gacttaaata ttctctttga tttacatagt  360
gaaactccat tcttgtttcc gaaattgtag tgtgtatagt ctagaaaatt aagaagtaga   420
caaaatgatt tatgagattg taaattgtag gctttttatc aatttattaa ttttagagac    480
caaaatttgc ctatccttatt tggaccaatt tattgtatgt taggatcgac atgagtttag  540
caaaatcatg acggcaccat gactgtgttg aagcttcttt gtgtaacttt aaccaaaatt   600
atatggcaca ccatgattat gcaaactcac cgtcaatcca acatagaaa ttcagtgtta   660 atctttgtga caataaaaaa ctatgagtta tgttgtacta atttatttcc attgtgaaac   720
tcagatggta gatttatgat gagactaaaa ctcccaaatg gggtaacaac aagtgctcaa   780
acaagatact tggcgagtgt gataaaaaaa tatggcaaag acggatgtgc tgatgtgaca   840
```

-continued

```
acgaggcaga attggcaaat tcgaggtgta acgttacctg atgtccctga aattcttaag      900
ggccttgcag aggtcggctt gacaagtctg cagagtggaa tggacaatgt tcgaaaccca      960
gttggtaacc ctcttgctgg tattgaccct gatgagattg ttgatacaag accttacacc     1020
aatttgctgt cccaattcat cactgctaat tcacttggta atccaaccat tacaaacttg     1080
taagtctaaa ctatctcatc tttatatttc actcattata tcatattagt agttagttac     1140
ttgcattgca agcattacgt gaccgtgtgt agcctctaaa tccttttgat aatatgtgca     1200
ggccaaggaa gtggaatgta tgtgtgatag gttcccatga tcttttcgag catccgcata     1260
ttaacgatct tgcttatatg cctgctaata aggatggtcg atttggattc aacttattgg     1320
tgggtggttt ctttagtccc aagcgatgtg ctgaagcagt tccacttgat gcatgggtct     1380
ctgcagatga tgttatccca ctttgtaaag ctgtccttga acctatagg gacctcggca      1440
caagagggaa tagacagaaa accagaatga tgtggttgat cgatgaactt gtaagttacc     1500
acttttttc ttcacatatt attaactgaa gtgactttaa cgaccatttt acaattgaaa      1560
tttaagtgga ttttagccct atcattacaa gaacaaattt gttaattcac tagcaagagc     1620
aattccactt tggcttggac atgacaagtg tttgtgaaat gcaggggata gaagtattca     1680
gatcagaggt ggaaaaaaga atgccagaga agaagctaga gagagcatcc aaagaagaac     1740
ttgtccaaaa acaatggaaa gaggagacat cttaggtgtt catccacaaa aacaagaagg     1800
tttaagctat gttggaattc acattccagt tggtagaatc caagcagatg agatggaaga     1860
gctagctcgt atcgccgatg aatacggaac cggagaacta aggctaaccg tggagcaaaa     1920
cataataatt ccaaatgtgg aaaactcaaa acttgatgca ttgctaaatg aacctctctt     1980
gaaagacaaa ttctcaccag aaccttccat cctaatgaaa acacttgtgg catgcactgg     2040
taaccaattt tgtggccaag caataattga aacaaaacaa agagctttaa agtaactga      2100
agaagttgaa agacatgtgg ctgtgagcaa accagtgaga atgcattgga ctggttgtcc     2160
taacacttgt ggtcaagttc aggttgctga tattggtttt atgggttgta tggctaggga     2220
tgagaatggt aaggctactg aaggtgttga tattttcctt ggtgggagaa ttggaagtga     2280
ttctcattta gctgaggtgt ataagaaagg tgtcccttgc aaggacttgg tgcctattgt     2340
agctgatatt ttggttaaat attttggagc tgtccaaagg aatagagaag aaggggatga     2400
ttaaagtata taggtatttg gtgattttaa ttgcctctac acaaaattat tatgttctgt     2460
ccaaaatata aagtcacaag ggataattga gattgagatg cagcacgcca cacatgaact     2520
tgtacatttg gataagtcat ttttcattgc tattttataa gttacacttt gaattttata     2580
ataaattta ttttatttca aggaccagat tttataagga aaccgctaat ctaactatct      2640
ttactcgtaa tttgtcattt gagagctacg gagatcgttg agtttacgta tgagtgttta     2700
gtctcacatt aattatgaat ggtcaaaatg ttaaatttat aagagatgta atctatatac     2760
ctaatgcatt aaaaatttgg atggagatgc gacgcccccc ttttttgtgg tcctgaagta     2820
tagacttgtt gtcgcttctg gtgcactctc atacttccca acaaggagaa aaaactacca     2880
taacaattaa caaactaaca tttgttattt aaaaaaacat acggatactg ttttttcccc     2940
atttattagg aagatgatgg cttggatttc aatggctgag tttatttttt ttttggtcgg     3000
gagttgaagt atcgggaaaa ctaaatatgc tatgacttta acattgtgt tgatatatga      3060
ttagtttca acttacttaa aaagtggcaa actagtttag tggttctctc ccttccttgt      3120
agttcaagga acatgggttt gaactctgtc caaattttg tactttcaat tatccataca      3180
tttaaaagct atataccaca tcattatatt caagtcaatg atcatgcggc ctgccacatt     3240
```

<210> SEQ ID NO 15
<211> LENGTH: 617
<212> TYPE: DNA
<213> ORGANISM: Artificial Sequence
<220> FEATURE:
<223> OTHER INFORMATION: Sequences to be used as terminator for regulating expression of foreign genes

<400> SEQUENCE: 15

```
agtatatagg tatttggtga ttttaattgc ctctacacaa aattattatg ttctgtccaa      60
aatataaagt cacaagggat aattgagatt gagatgcagc acgccacaca tgaacttgta     120
catttggata agtcattttt cattgctatt ttataagtta cactttgaat tttataataa     180
atttattttt atttcaagga ccagatttta taaggaaacc gctaatctaa ctatctttac     240
tcgtaatttg tcatttgaga gctacggaga tcgttgagtt tacgtatgag tgtttagtct     300
cacattaatt atgaatggtc aaaatgttaa atttataaga gatgtaatct atatacctaa     360
tgcattaaaa atttggatgg agatgcgacg cccccctttt ttgtggtcct gaagtataga     420
cttgttgtcg cttctggtgc actctcatac ttcccaacaa ggagaaaaaa ctaccataac     480
aattaacaaa ctaacatttg ttatttaaaa aaacatacgg atactgtttt ttccccattt     540
attaggaaga tgatggcttg gatttcaatg gctgagttta ttttttttttt ggtcgggagt     600
tgaagtatcg ggaaaac                                                   617
```

<210> SEQ ID NO 16
<211> LENGTH: 502
<212> TYPE: DNA
<213> ORGANISM: Artificial Sequence
<220> FEATURE:
<223> OTHER INFORMATION: Sequences to be used as terminator for regulating expression of foreign genes

<400> SEQUENCE: 16

```
ttgtacattt ggataagtca tttttcattg ctatttttata agttacactt tgaattttat      60
aataaattttt attttatttc aaggaccaga ttttataagg aaaccgctaa tctaactatc     120
tttactcgta atttgtcatt tgagagctac ggagatcgtt gagtttacgt atgagtgttt     180
agtctcacat taattatgaa tggtcaaaat gttaaattta agagatgt aatctatata     240
cctaatgcat taaaaatttg gatggagatg cgacgccccc cttttttgtg gtcctgaagt     300
atagacttgt tgtcgcttct ggtgcactct catacttccc aacaaggaga aaaaactacc     360
ataacaatta acaaactaac atttgttatt taaaaaaaca tacggatact gttttttccc     420
catttattag gaagatgatg gcttggattt caatggctga gtttattttt ttttggtcg     480
ggagttgaag tatcgggaaa ac                                             502
```

<210> SEQ ID NO 17
<211> LENGTH: 25
<212> TYPE: DNA
<213> ORGANISM: Artificial Sequence
<220> FEATURE:
<223> OTHER INFORMATION: Sequences to be used as primers -continued

<400> SEQUENCE: 17
gatattgatg ttagactcaa gtggc                                              25

<210> SEQ ID NO 18
<211> LENGTH: 21
<212> TYPE: DNA
<213> ORGANISM: Artificial Sequence
<220> FEATURE:
<223> OTHER INFORMATION: Sequences to be used as primers

<400> SEQUENCE: 18
cacysattcc acttcctwgg c                                                  21

<210> SEQ ID NO 19
<211> LENGTH: 27
<212> TYPE: DNA
<213> ORGANISM: Artificial Sequence
<220> FEATURE:
<223> OTHER INFORMATION: Sequences to be used as primers

<400> SEQUENCE: 19
ttgtcacatc agcacatccg tctttgc                                            27

<210> SEQ ID NO 20
<211> LENGTH: 27
<212> TYPE: DNA
<213> ORGANISM: Artificial Sequence
<220> FEATURE:
<223> OTHER INFORMATION: Sequences to be used as primers

<400> SEQUENCE: 20
tcgccaagta tcttgtttga gcacttg                                            27

<210> SEQ ID NO 21
<211> LENGTH: 27
<212> TYPE: DNA
<213> ORGANISM: Artificial Sequence
<220> FEATURE:
<223> OTHER INFORMATION: Sequences to be used as primers

<400> SEQUENCE: 21
agagcccggg agaagagagt gtgtttg                                            27

<210> SEQ ID NO 22
<211> LENGTH: 28
<212> TYPE: DNA
<213> ORGANISM: Artificial Sequence
<220> FEATURE:
<223> OTHER INFORMATION: Sequences to be used as primers

<400> SEQUENCE: 22
ttctcccggg ggacgagaga tggatggt                                           28

<210> SEQ ID NO 23
<211> LENGTH: 30
<212> TYPE: DNA
<213> ORGANISM: Artificial Sequence
<220> FEATURE:
<223> OTHER INFORMATION: Sequences to be used as primers

<400> SEQUENCE: 23
ttctcccggg gttgaaacag gtgcaactga                                         30

<210> SEQ ID NO 24
<211> LENGTH: 28

```
<212> TYPE: DNA
<213> ORGANISM: Artificial Sequence
<220> FEATURE:
<223> OTHER INFORMATION: Sequences to be used as primers

<400> SEQUENCE: 24
ttctcccggg taaccatctt tttcctca                                    28

<210> SEQ ID NO 25
<211> LENGTH: 24
<212> TYPE: DNA
<213> ORGANISM: Artificial Sequence
<220> FEATURE:
<223> OTHER INFORMATION: Sequences to be used as primers

<400> SEQUENCE: 25
cacacttctt cactcacctc tcaa                                        24

<210> SEQ ID NO 26
<211> LENGTH: 21
<212> TYPE: DNA
<213> ORGANISM: Artificial Sequence
<220> FEATURE:
<223> OTHER INFORMATION: Sequences to be used as primers

<400> SEQUENCE: 26
atctaggagg ggcagacatt g                                           21

<210> SEQ ID NO 27
<211> LENGTH: 24
<212> TYPE: DNA
<213> ORGANISM: Artificial Sequence
<220> FEATURE:
<223> OTHER INFORMATION: sequences to be used as primers

<400> SEQUENCE: 27
tcggtataaa gacttcgcgc tgat                                        24

<210> SEQ ID NO 28
<211> LENGTH: 27
<212> TYPE: DNA
<213> ORGANISM: Artificial Sequence
<220> FEATURE:
<223> OTHER INFORMATION: sequences to be used as primers

<400> SEQUENCE: 28
atgtcttcct tctcagtacg tttcctc                                     27

<210> SEQ ID NO 29
<211> LENGTH: 30
<212> TYPE: DNA
<213> ORGANISM: Artificial Sequence
<220> FEATURE:
<223> OTHER INFORMATION: sequences to be used as primers

<400> SEQUENCE: 29
caagttgatg catcaaggtg ggagcctaga                                  30

<210> SEQ ID NO 30
<211> LENGTH: 30
<212> TYPE: DNA
<213> ORGANISM: Artificial Sequence
<220> FEATURE:
<223> OTHER INFORMATION: sequences to be used as primers
```

```
<400> SEQUENCE: 30
agaagagctc agtatatagg tatttggtga                                        30

<210> SEQ ID NO 31
<211> LENGTH: 30
<212> TYPE: DNA
<213> ORGANISM: Artificial Sequence
<220> FEATURE:
<223> OTHER INFORMATION: sequences to be used as primers

<400> SEQUENCE: 31
agaagagctc ttgtacattt ggataagtca                                        30

<210> SEQ ID NO 32
<211> LENGTH: 30
<212> TYPE: DNA
<213> ORGANISM: Artificial Sequence
<220> FEATURE:
<223> OTHER INFORMATION: sequences to be used as primers

<400> SEQUENCE: 32
agaagaattc gttttcccga tacttcaact                                        30
```